(12) United States Patent
Ramamurthi et al.

(10) Patent No.: US 9,675,560 B2
(45) Date of Patent: Jun. 13, 2017

(54) NANOPARTICLES FOR CONTROLLED LYSIS OF BLOOD CLOTS

(71) Applicant: THE CLEVELAND CLINIC FOUNDATION, Cleveland, OH (US)

(72) Inventors: Anand Ramamurthi, Pepper Pike, OH (US); Balakrishnan Sivaraman, Westlake, OH (US); Andrew Sylvester, Richmond, VA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/471,616

(22) Filed: Aug. 28, 2014

(65) Prior Publication Data

US 2015/0064267 A1 Mar. 5, 2015

Related U.S. Application Data

(60) Provisional application No. 61/870,827, filed on Aug. 28, 2013.

(51) Int. Cl.
*A61K 38/48* (2006.01)
*A61K 9/51* (2006.01)
*A61K 9/14* (2006.01)
*A61K 47/48* (2006.01)

(52) U.S. Cl.
CPC .............. *A61K 9/5153* (2013.01); *A61K 9/14* (2013.01); *A61K 47/48023* (2013.01); *A61K 47/48915* (2013.01)

(58) Field of Classification Search
None
See application file for complete search history.

(56) References Cited

U.S. PATENT DOCUMENTS

| 2010/0272740 A1* | 10/2010 | Vertegel | A61K 38/49 424/178.1 |
| 2012/0177741 A1* | 7/2012 | Moslemy | A61K 9/0048 424/489 |
| 2012/0177742 A1* | 7/2012 | McClain | B82Y 5/00 424/490 |

FOREIGN PATENT DOCUMENTS

WO 2009052367 A1 4/2009

OTHER PUBLICATIONS

Scott et al., Arterioscler Thromb Vasc Biol, 2001, 31, 3004-3010.*
Song et al., Journal of Controlled Release, 1998, 54, 201-211.*
Park et al., Journal of Controlled Release, 2001, 75, 37-44.*
Ahmann, Katherine A., et al. "Fibrin degradation enhances vascular smooth muscle cell proliferation and matrix deposition in fibrin-based tissue constructs fabricated in vitro." Tissue Engineering Part A 16.10 (2010): 3261-3270.
Andersen, Henning R., et al. "A comparison of coronary angioplasty with fibrinolytic therapy in acute myocardial infarction." New England Journal of Medicine 349.8 (2003): 733-742.
Carmeliet, Peter, et al. "Urokinase-generated plasmin activates matrix metalloproteinases during aneurysm formation." Nature genetics 17.4 (1997): 439-444.
Chapman, H. A., and O. L. Stone. "Co-operation between plasmin and elastase in elastin degradation by intact murine macrophages." Biochem. j 222 (1984): 721-728.
Chen, Fa-Ming, et al. "Novel glycidyl methacrylated dextran (Dex-GMA)/gelatin hydrogel scaffolds containing microspheres loaded with bone morphogenetic proteins: formulation and characteristics." Journal of controlled release 118.1 (2007): 65-77.
Chesebro, J. H., et al. "Thrombolysis in Myocardial Infarction (TIMI) Trial, Phase I: A comparison between intravenous tissue plasminogen activator and intravenous streptokinase. Clinical findings through hospital discharge." Circulation.76.1 (1987): 142-154.
Chung, Tze-Wen, Shoei-Shen Wang, and Wei-Jain Tsai. "Accelerating thrombolysis with chitosan-coated plasminogen activators encapsulated in poly-(lactide-co-glycolide)(PLGA) nanoparticles." Biomaterials 29.2 (2008): 228-237.
Collet, J. P., et al. "Influence of fibrin network conformation and fibrin fiber diameter on fibrinolysis speed dynamic and structural approaches by confocal microscopy." Arteriosclerosis, Thrombosis, and Vascular Biology 20.5 (2000): 1354-1361.
Daugherty, Alan, and Lisa A. Cassis. "Mechanisms of abdominal aortic aneurysm formation." Current atherosclerosis reports 4.3 (2002): 222-227.
Di Martino, E., et al. "Biomechanics of abdominal aortic aneurysm in the presence of endoluminal thrombus: experimental characterisation and structural static computational analysis." European Journal of Vascular and Endovascular Surgery 15.4 (1998): 290-299.
Gertler, Arieh, and Gad Feinstein. "Inhibition of porcine elastase by turkey ovomucoid and chicken ovoinhibitor." European Journal of Biochemistry 20.4 (1971): 547-552.
Kazi, Monsur, et al. "Influence of intraluminal thrombus on structural and cellular composition of abdominal aortic aneurysm wall." Journal of vascular surgery 38.6 (2003): 1283-1292.
Labhasetwar, Vinod, et al. "Arterial uptake of biodegradable nanoparticles: effect of surface modifications." Journal of pharmaceutical sciences 87.10 (1998): 1229-1234.
Leach, J. Kent, et al. "Accelerated thrombolysis in a rabbit model of carotid artery thrombosis with liposome-encapsulated and micro-encapsulated streptokinase." Thromb Haemost 90.1 (2003): 64-70.
Lijnen, H. R. "Plasmin and matrix metalloproteinases in vascular remodeling." Thromb Haemost 86.1 (2001): 324-33.
Narang, Ajit S., David Delmarre, and Danchen Gao. "Stable drug encapsulation in micelles and microemulsions." International journal of pharmaceutics 345.1 (2007): 9-25.
Roztocil, Elisa, et al. "Plasmin-induced smooth muscle cell proliferation requires epidermal growth factor activation through an extracellular pathway." Surgery 138.2 (2005): 180-186.

(Continued)

*Primary Examiner* — Abigail Fisher
(74) *Attorney, Agent, or Firm* — Tarolli, Sundheim, Covell & Tummino LLP

(57) ABSTRACT

Fibrinolytic nanoparticles including a polymeric core having a surface that is functionalized with a cationic amphiphilic compound, and a fibrinolytic agent dispersed within the core, are described herein. The fibrinolytic nanoparticles can be used in method of dissolving a blood clot in a subject by administering to the subject a therapeutically effective amount of fibrinolytic nanoparticles.

9 Claims, 12 Drawing Sheets

(56) References Cited

OTHER PUBLICATIONS

Shaltoni, Hashem M., et al. "Is intra-arterial thrombolysis safe after full-dose intravenous recombinant tissue plasminogen activator for acute ischemic stroke?." Stroke 38.1 (2007): 80-84.

Stenbaek, J., B. Kalin, and J. Swedenborg. "Growth of thrombus may be a better predictor of rupture than diameter in patients with abdominal aortic aneurysms." European Journal of Vascular and Endovascular Surgery 20.5 (2000): 466-469.

Sylvester, Andrew, et al. "Nanoparticles for localized delivery of hyaluronan oligomers towards regenerative repair of elastic matrix." Acta biomaterialia 9.12 (2013): 9292-9302.

Touat, Ziad, et al. "Renewal of mural thrombus releases plasma markers and is involved in aortic abdominal aneurysm evolution." The American journal of pathology 168.3 (2006): 1022-1030.

Venkataraman, Lavanya, et al. "Nanoparticulate delivery of agents for induced elastogenesis in three-dimensional collagenous matrices." Journal of tissue engineering and regenerative medicine (2014).

Vorp, David A., et al. "Association of intraluminal thrombus in abdominal aortic aneurysm with local hypoxia and wall weakening." Journal of Vascular Surgery 34.2 (2001): 291-299.

Wang, Shoei-Shen, Nai-Kuan Chou, and Tze-Wen Chung. "The t-PA-encapsulated PLGA nanoparticles shelled with CS or CS-GRGD alter both permeation through and dissolving patterns of blood clots compared with t-PA solution: An in vitro thrombolysis study." Journal of Biomedical Materials Research Part A 91.3 (2009): 753-761.

Wolberg, Alisa S. "Thrombin generation and fibrin clot structure." Blood reviews 21.3 (2007): 131-142.

Wu, Jung-He, Khalid Siddiqui, and Scott L. Diamond. "Transport phenomena and clot dissolving therapy: an experimental investigation of diffusion-controlled and permeation-enhanced fibrinolysis." Thrombosis and haemostasis 72.1 (1994): 105-112.

Yang, Zhe, et al. "Effect of tissue plasminogen activator on vascular smooth muscle cells." Journal of vascular surgery 42.3 (2005): 532-538.

\* cited by examiner

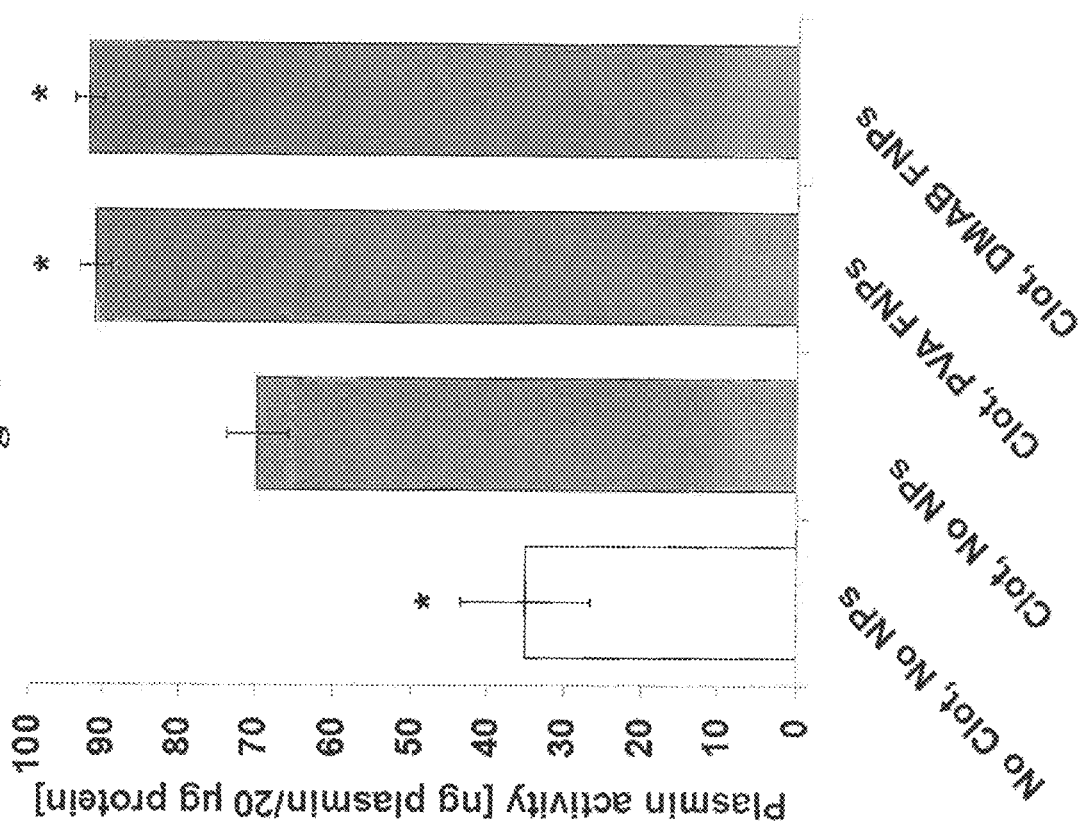

NANOPARTICLES FOR CONTROLLED LYSIS OF BLOOD CLOTS

CROSS-REFERENCE TO RELATED APPLICATIONS

This application claims the benefit of U.S. Provisional Application No. 61/870,827, filed Aug. 28, 2013, which is incorporated herein by reference.

GOVERNMENT FUNDING

This invention was made with government support under HL092051 awarded by the National Institutes of Health. The government has certain rights in the invention.

BACKGROUND

Abdominal aortic aneurysms (AAAs) cause 1-3% of all deaths among men between the ages of 65-85 in developed nations. The condition is characterized by chronic enzymatic disruption and progressive loss of the extracellular matrix (ECM), particularly the elastic matrix, within the wall of the infrarenal abdominal aorta, leading to its slow expansion and weakening, to culminate in fatal rupture. (Selle et al., Ann Surg. 189:158-64 (1979)). The matrix metalloproteinases (MMPs)-2 and -9, which are overexpressed by inflammatory cells recruited to the AAA site, as well as activated aortic smooth muscle cells (SMCs) at the AAA site, have been shown to cause elastin breakdown, thereby driving AAA growth. (Daugherty A, Cassis L A., Curr Atheroscler Rep. 4:222-7 (2002)). Unfortunately, auto-repair and/or regeneration of elastic matrix by adult vascular cells, and more so diseased aneurysmal cells, is very poor. Additionally, since they are incapable of efficiently recruiting, cross-linking and organizing elastin precursors into a mature fiber-based matrix, reversal of AAA pathology is not possible. This prospect is also further diminished by the apoptosis of SMCs within the elastic medial layer of the aorta, and the chronic overexpression of MMPs due to which net accumulation of the limited de novo synthesized elastic matrix is poor.

Greater than 90% of AAAs in humans tend to be detected when they are still small (i.e., their maximal diameter is less than 5.5 cm), and have a slow growth rate (<10% per year). However, they tend to be surgically or minimally invasively treated only when they attain a size greater than 5.5 cm, when they have high risk of rupture. (Lederle et al., Arch Intern Med.; 160:1425-30 (2000)). Since many elderly patients are unfit for surgery, there is a strong but unmet need for pathophysiologically-based non-surgical therapies that may be applied during the >5 years passive monitoring of small, growing AAAs, before they attain a size at which the rupture risk outweighs the surgical risk.

An intraluminal thrombus (ILT) is present in ~75% of all AAAs, and is a critical pathophysiological determinant of AAA growth, although its exact role in AAA progression has remained contradictory. While some studies have suggested that the ILT is 'inert' and shields the underlying wall from hemodynamic stresses, others have shown it to mediate proteolytic changes in the aortic wall that lead to AAA growth and rupture. (Vorp et al., J Vasc Surg. 34:291-9 (2001)). Additionally, studies have shown a strong correlation between ILT size, AAA growth, and the risk of rupture, leading to its recognition as an important indicator of AAA progression. (Stenbaek et al., European Journal of Vascular and Endovascular Surgery. 20:466-9 (2000)). Based on the varied roles of the ILT in AAA progression and its likely impediment to the diffusion of oxygen and delivered therapeutics from the bloodstream into the AAA wall, there is a critical need to develop approaches to render the clots porous or to lyse them. Thrombolysis following intravenous administration of tissue plasminogen activator (tPA) has been shown to be effective in rapidly restoring blood flow in patients following thrombotic events such as stroke (Shaltoni et al., Stroke, 38:80-4 (2007)) and myocardial infarction (MI) (Chesebro et al., Circulation. 76:142-54 (1987). It converts plasminogen in the bloodstream into its active plasmin form, which then circulates systemically and mediates thrombolysis. However, high systemic plasmin levels lead to enhanced MMP expression (Lijnen H R, Thromb Haemost. 86:324-33 (2001)) and elastin/elastic matrix degradation (Chen et al., J Control Release. 118:65-77 (2007)), which are undesirable in an AAA scenario. Additionally, rapid clot lysis may be undesirable from the standpoints of (a) sudden exposure of the underlying aortic wall to proteases and inflammatory cells present in the ILT, and (b) loss of its (bio)mechanical shielding effect on the underlying wall. Therefore, there is a critical need for methods to enable slow and controlled thrombolysis to modulate plasmin production, minimize systemic plasminemia, and prevent AAA rupture.

On account of systemic plasminemia associated with systemic delivery and doses of plasminogen activators, studies have examined the development of nanoparticle (NP)-based controlled release systems. This is due to the fact that tPA also acts upon plasminogen in circulation generating systemic plasmin and rendering the treated patient highly vulnerable to hemorrhage. Newer products that have been developed such as micro- and nanoscale devices for delivery of active fibrinolytic agents focus on delivering tPA to a blood clot for postmyocardial infarction or ischemic stroke treatment using nanoparticles. See PCT publication WO/2009/052367. These fibrinolytic nanoparticles attempt to minimize systemic plasminemia compared to the use of free tPA. However, these nanoparticle delivery systems can still result in rapid and relatively uncontrolled lysis of the clot.

SUMMARY

To fulfill the above need, the inventors have investigated the controlled release of tPA from poly(lactic-co-glycolic acid) nanoparticles (PLGA NPs) as a potential modality for gradual lysis of fibrin clots. They also evaluated the effects of anionic and cationic surface functionalization of the NPs on their clot binding abilities, as well as functional effects of tPA release and fibrinolytic products on the cell proliferation, elastic matrix deposition, MMP-synthesis and enzyme activity, and plasmin activity within aneurysmal rat aortic SMC (EaRASMC) cultures. One of the primary goals was to achieve gradual clot lysis using minimal tPA dosing, so as to limit plasmin production and activation, with an eye towards preserving the elastic matrix in the AAA wall and preventing increases in local MMP synthesis and activity. While complete clot lysis is not necessarily the ultimate goal, the nanoparticles of the present invention increase the permeability of the clot (via partial lysis due to the controlled delivery of tPA), enabling the subsequent transmural transport of endolumenally infused matrix regenerative/anti-proteolytic AAA therapeutics (cell- or NP-based) to the AAA wall.

The inventors have developed nanoparticles (NPs) for effecting controlled fibrinolysis in AAAs. These nanoparticles are able to partially lyse a blood clot in a controlled manner to such an extent as to render the clot porous enough to enable uptake of other delivered AAA therapeutics, while potentially continuing to mechanically shield the AAA wall from hemodynamic stresses. This is potentially ideal for AAA treatment and the opposite of the desired effect in other applications where rapid and full clot lysis occurs. In addition, surface modification of the nanoparticles has the added benefit of allowing for targeting clots in a new way.

The nanoparticles of the present invention are able to provide controlled thrombolysis compared to current applications and technologies of both exogenous tPA delivered intravenously and other thrombolytic NP formulations. The inventors' approach allows the positively-charged NPs to permeate into the clot and bind to the negatively-charged fibrin and form pores in the clot that can be controlled to allow for a desired loss of thrombus volume as well as control the speed of thrombolysis in order to prevent an embolism or other possible negative side effects.

BRIEF DESCRIPTION OF THE FIGURES

FIG. 12 provides a graph showing plasmin activity in EaRASMC layers (measured per 20 µg of harvested cell layer protein incubated with chromogenic plasmin synthetic substrate S-2403 for 24 h) following exposure to tPA and fibrinolytic products released upon lysis of a fibrin clot by PVA- and DMAB-FNPs (loaded with 10 µg tPA) at 0.5 mg/mL NP concentration in a transwell culture (Clot+NPs in insert, EaRASMCs in wells). Data shown indicates mean±SD; n=3/case, * denotes p<0.05 compared to unlysed clot control (No Clot, No NP).

DETAILED DESCRIPTION

Figure 1:
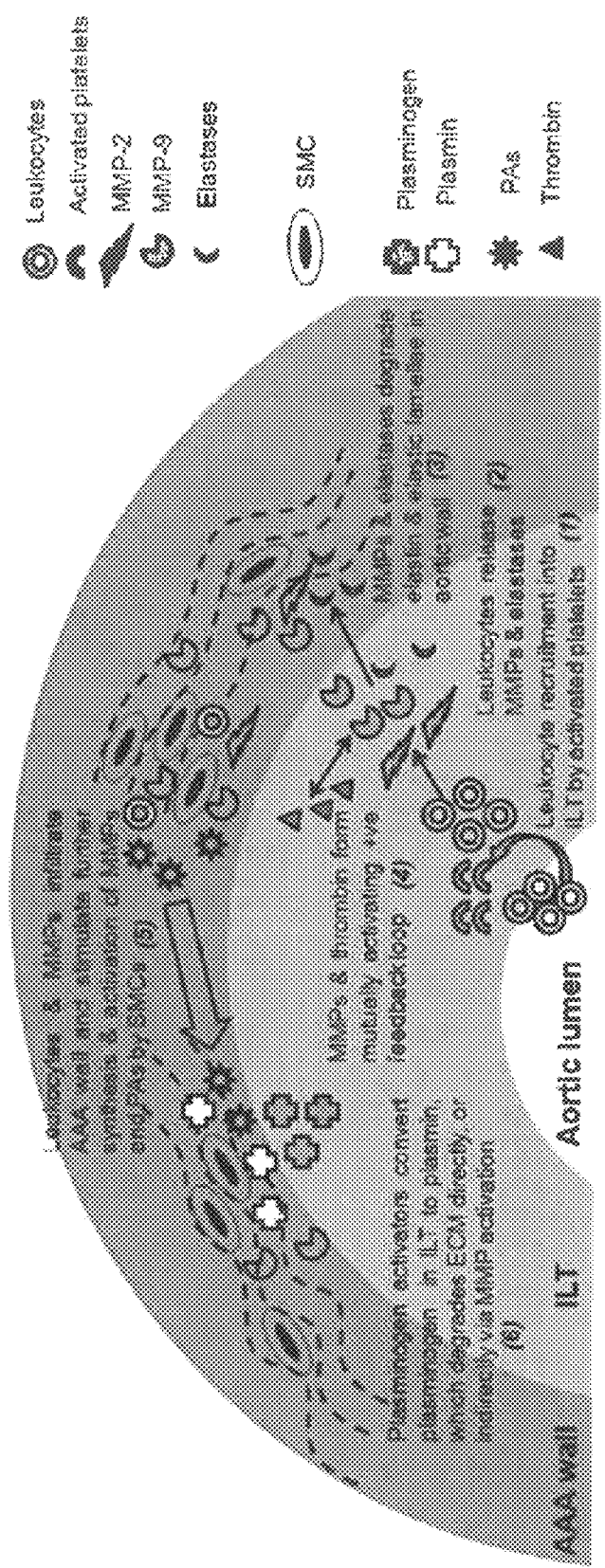
FIG. 1 provides a schematic illustration of the potential role played by the intraluminal thrombus (ILT) in AAA progression. It serves as a reservoir of inflammatory cells (platelets and leukocytes) and proteases (plasmin/plasminogen, MMPs, elastases). These cells and proteases infiltrate into the tunica media of the aortic wall, where they degrade elastin and elastic lamellae. Further, they activate aortic SMCs, stimulating the secretion and activation of MMPs and plasminogen activators (PAs). PAs then convert plasminogen within the ILT to its active form, plasmin, which directly degrades elastin within the aortic wall, or activates MMPs to induce further elastin and elastic matrix degradation.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

DEFINITIONS

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

The language "effective amount" or "therapeutically effective amount" refers to a nontoxic but sufficient amount of the composition used in the practice of the invention that is effective to enable the degree of controlled clot lysis, restore and preserve architecturally appropriate elastic matrix, and at the minimum not be conducive to enhancing proteolytic activity at the site of tissue delivery. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

Figure 2:
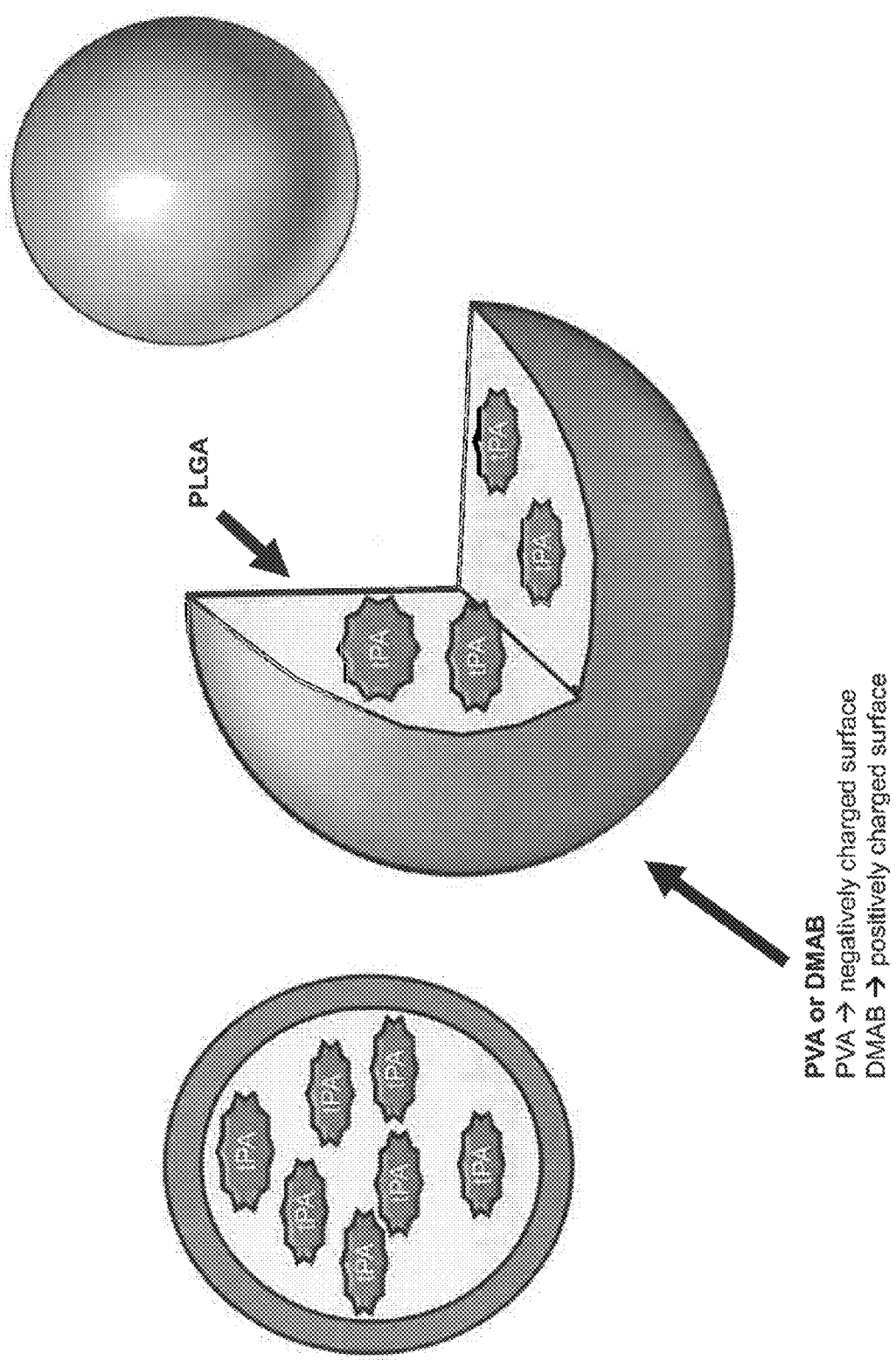
FIG. 2 provides a schematic representation of the fibrinolytic nanoparticles (FNPs). The fibrinolytic drug (tissue plasminogen activator or tPA) was encapsulated within poly(lactic-co-glycolic acid) (PLGA) via a double emulsion/ solvent evaporation technique. These nanoparticles were functionalized during the emulsification process with either (a) a non-ionic stabilizer (polyvinyl alcohol or PVA) that imparts them with a negative surface charge, or (b) a cationic stabilizer (dodidecyldimethylammonium bromide or DMAB) that imparts them with a positive surface charge.

In one aspect, the present invention provides a fibrinolytic nanoparticle (NP) that includes a polymeric core having a surface that is preferably functionalized with a cationic amphiphilic compound, and includes a fibrinolytic agent dispersed within the polymeric core. Functionalized, as the term is used herein, refers to modification of the surface of the polymeric core of the NPs by attachment of a compound that varies the function of the NP. A schematic representation of the nanoparticles of the invention is provided in FIG. 2. As can be seen in the figure, the fibrinolytic nanoparticles have three components: a polymeric core, a fibrinolytic agent dispersed within the polymer core, and an outer layer of cationic amphiphilic compounds, which can be referred to as the functionalization layer, that is present on the surface of the polymeric core.

Nanoparticles, as the term is used herein, are particles having a size of 1000 nanometers or less. In some embodiments, the particles have a diameter from about 100 nanometers to about 1000 nanometers. In other embodiments, the particles have a diameter from about 200 nanometers to about 500 nanometers. In further embodiments, the particles have a diameter from about 300 to about 500 nanometers, while in yet further embodiments the particles have a diameter from about 350 to about 450 nanometers. The diameter of the nanoparticles refers to their mean hydrodynamic diameter. The hydrodynamic diameter is the measurement that includes the polymeric core along with the functionalization layer and a solvent layer that associates with the nanoparticle. The hydrodynamic diameter can be readily determined using dynamic light scattering (DLS).

The polymer core of the nanoparticles can be formed from one or more natural or synthetic polymers such as, without limitation, polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like. In a preferred embodiment, the polymeric core comprises poly(lactic-co-glycolic acid).

The polymeric core of the nanoparticles encapsulates a fibrinolytic agent that is dispersed within the core. Preferably the fibrinolytic agent is substantially evenly dispersed throughout the core. Any suitable fibrinolytic agent can be used. Fibrinolytic agents are compounds that dissolve blood clots by activating plasminogen to plasmin. Plasmin formation and/or activation leads to the degradation of fibrin to accomplish fibrinolysis, and thereby clot dissolution. For example, the fibrinolytic agent can be tissue plasminogen activator (tPA), streptokinase (SK), or urokinase (UK). Preferably the fibrinolytic agent is tissue plasminogen activator. Examples of tissue plasminogen activators include Alteplase (a recombinant form of tPA), Retaplase (a smaller derivative of recombinant tPA), and Tenecteplase, which has a longer half-life and greater binding affinity for fibrin.

In some embodiments of the fibrinolytic nanoparticles provided herein, the weight/weight (w/w) percent of the fibrinolytic agent in the encapsulated active agent nanoparticles is about 5%. In some embodiments, the w/w percent of the fibrinolytic agent in the encapsulated active agent nanoparticles is about 2-10%.

The surface of the polymer core is preferably functionalized with cationic amphiphilic compounds. The cationic amphiphilic compounds should be biocompatible and suitable for providing a significant amount of positive charge to the nanoparticle. Cationic amphiphiles are preferable from the standpoint of targeted binding of NPs to the fibrin clot, obtaining even lower and more gradual tPA release and thus slower clot lysis deven relative to the negatively charged NPs, for providing anti-MMP activity in a plasmin rich microenvironment, and also from the standpoint of enabling an outside-in pattern of clot lysis. In some embodiments, the nanoparticles have a surface charge from about +10 mV to about +50 mV. In other embodiments, the nanoparticles have a surface charge from about +20 mV to about +40 mV, while in further embodiments the nanoparticles have a surface charge from about +30 mV to about +35 mV.

Cationic amphiphilic compounds are organic compounds including a positive charge and have an amphiphilic character. Amphiphilic character refers to a compound having a polar water-soluble group attached to a water-insoluble hydrocarbon chain, as is found in surfactant molecules. In some embodiments, the positive charge is provided by a quaternary ammonium group. Examples of cationic amphiphilic compounds include dimethyldioctadecylammonium chloride; dioctadecyldimethylammonium bromide (DODAB), didodecyldimethylammonium bromide (DMAB), dodecylamine hydrochloride (DAH), docecyltrimethyl ammonium bromide (DTAB), linear isoform polyethylenimine (linear PEI), branched low MW polyethylenimine (PEI) (of about <25 KDa), branched Low MW polyethylenimine (PEI) (of about <15 KDa), branched Low MW polyethylenimine (PEI) (of about <10 KDa), branched high MW polyethylenimine (of about >1-25 KDa), poly-L-arginine (average or nominal MW of about 70,000 Da), poly-L-arginine (average or nominal MW>about 50,000 Da), poly-L-arginine (average or nominal MW of about 5,000 to about 15,000 Da), poly-L-lysine (average or nominal MW of about 28,200 Da), poly-L-lysine (average or nominal MW of about 67,000 Da), poly histidine, ethylhexadecyldimethylammonium bromide, dodecyltrimethyl ammonium bromide, tetradodecyl ammonium bromide, dimethylditetradecyl ammonium bromide, tetrabutylammonium iodide, DEAE-dextran hydrochloride, and hexadimethrine bromide. A preferred cationic amphiphilic compound is didodecyldimethyl ammonium bromide (DMAB).

While preferred embodiments of the invention include nanoparticles that are functionalized with cationic amphiphilic compounds, for the reasons described herein, some embodiments of the invention are directed to nanoparticles that are modified with a non-ionic surfactant, which as PVA, which maintains the negative charge of PLGA (about −35 mV). While not having all of the advantages of cationic amphiphilic functionalization, nanoparticles modified with non-ionic surfactants can be effective in some scenarios.

Another aspect of the invention provides a method of dissolving a blood clot in a subject by administering to the subject a therapeutically effective amount of the fibrinolytic nanoparticles described herein. The fibrinolytic nanoparticles include a polymeric core having a surface that is functionalized with a cationic amphiphilic compound, and a fibrinolytic agent dispersed within the core, and can include any of the various embodiments of the nanoparticles described herein.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

In some embodiments, the subject has been characterized as being in need of having a blood clot dissolved. A blood clot (a.k.a. thrombus) is the product of hemostasis resulting from platelet aggregation within a fibrin clot, and while useful in cases of injury, it is pathological in instances of thrombosis. Blood clots can occur in a variety of medical conditions, many of which are life threatening. For example, blood clots can occur in deep vein thrombosis, where they can embolize to flow through the heart and into the lungs where they form a pulmonary embolism. Blood clots can also form an arterial thrombus, causing a heart attack, stroke, or peripheral vascular disease, depending on whether the thrombus forms in the coronary arteries, arteries of the brain, or arteries of the leg, respectively. Blood clots can also form in abdominal aortic aneurysms, as described herein, where it is important not to dissolve the blood clot too rapidly since the blood clot, of which fibrin is a major component, particularly within AAAs, can contribute to the mechanical shielding of the weakened abdominal aorta. Accordingly, in some embodiments, the subject may be in need of having a blood clot dissolved more slowly than will occur if the subject is treated with prior art fibrinolytic methods.

Figure 3:
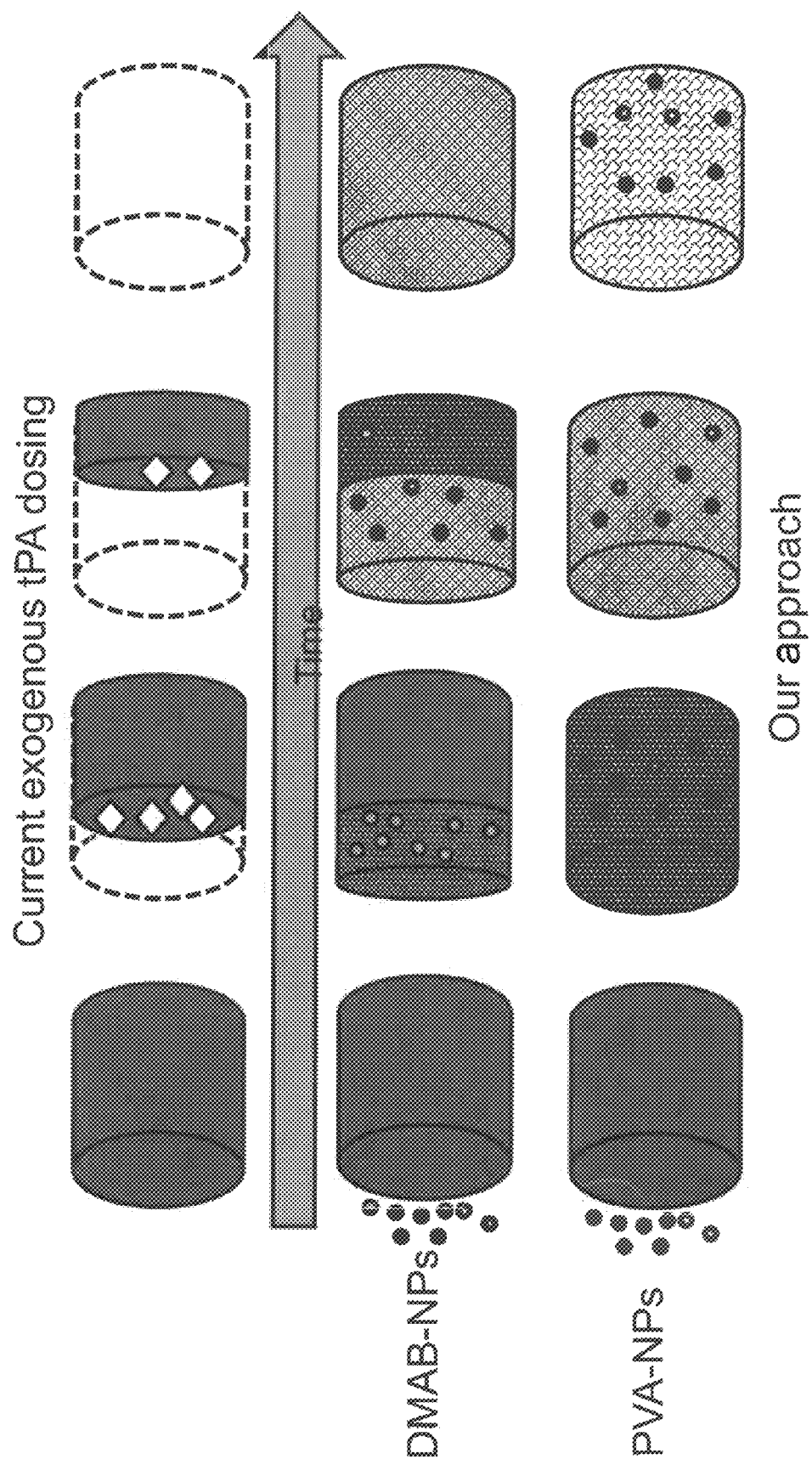
FIG. 3 provides a schematic representation showing that exogenous IV dosing of tPA leads to clot lysis in a manner that proceeds as a front (due to the affinity of tPA for fibrin), and completely lyses the clot as it comes in contact with the tPA. Similarly, due to the electrostatic binding of the cationic DMAB-functionalized fibrinolytic NPs to the (negatively charged) fibrin within the clot, clot lysis with these NPs proceeds more slowly as a front due to more controlled, gradual release of tPA from the NPs, leading to slow pore formation within the clot over time. Differently, the anionic PVA functionalized NPs become distributed throughout the clot and release tPA, again, in a gradual manner, from within the clot, leading to pore formation throughout the clot over time.

The present invention provides a controlled, more gradual lysis (i.e., dissolving) of the clot, which differs from previous work that focused on rapid thrombolysis in diseases such as in AAAs. Providing a controlled lysis of the clot has several advantages, such as avoiding systemic thrombotic/thromboembolic effects due to rapid clot lysis, minimizing the potential deleterious effects of clot and clot lysis products such as thrombin, MMPs and plasmin on degradation of aortic wall matrix, which could then potentially lead to further AAA growth, and avoiding the sudden loss of mechanical shielding effect of ILT on AAA wall. See FIG. 3.

Accordingly, various embodiments of the invention can dissolve a blood clot in various amounts of time. The time at which a clot is considered to be dissolved as the time at which the majority of the thrombus has disintegrated, but it is not necessary for 100% of the blood clot to be removed. In some embodiments, the method will require at least two hours to dissolve the blood clot. In other embodiments, the method takes at least 4 hours to dissolve the blood clot. In further embodiments, the method takes at least 8, 16, or 24 hours to dissolve the blood clot. In additional embodiments, the method will dissolve the blood clot within a certain range of time, such as from about 2 to about 8 hours, or from about 4 to about 16 hours.

The surface functionalization of the NPs with cationic amphiphilic compounds (such as DMAB) also provides a number of advantages, such as slower tPA release, enhanced clot binding or targeting, via electrostatic interactions with the negatively charged fibrin in the clot, and more gradual/controlled clot lysis, which may be attributed to the slower tPA release. The inventors have found that gradual/controlled clot lysis using NPs loaded with at least 10 µg tPA does not increase levels of MMP-synthesis and activity compared to exogenous delivery of tPA, when tested within aneurysmal SMC cultures. When NPs are loaded with higher amount of tPA (e.g., 20 µg), they were found to attenuate MMP synthesis and activity within aneurysmal SMC cultures.

Use of fibrinolytic NPs as a primary therapy could potentially lead to attenuation of intraluminal thrombus growth, which is a significant factor in AAA rupture, and reduced activation and/or infiltration of inflammatory cells and proteases, which would lead to attenuation of AAA growth. Additionally, the functionalization of the NPs with cationic long-chain compounds would also provide benefits with regards to (i) elastogenic outcomes and (ii) MMP-inhibitory outcomes, based on our preliminary results in vitro with aneurysmal SMC cultures.

The more gradual clot lysis profiles observed with the NPs of the present invention could avoid any negative events arising out of the sudden change in mechanical/hemo-dynamics within the vessel due to the sudden removal of the clot and its possible mechano-protective role on the underlying AAA tissue. Additionally, it could also facilitate regeneration of the underlying tissue.

In some embodiments, the delivery of anti-platelet therapy, either after or in conjunction with these fibrinolytic NPs, could be beneficial. Anti-platelet therapy may be dosed either orally, or encapsulated within and/or conjugated with NPs to ensure controlled delivery/bioavailability.

In addition, the delivery of fibrinolytic NPs as a first level therapy can enhance the porous nature of the clot, thereby enabling enhanced permeation and uptake of secondary therapeutics. For example, in one embodiment, NPs encapsulating an MMP-inhibitor, such as DOX which has been used as a therapeutic agent in vivo in animal and human AAA models, could be included in the NPs. In other embodiments, NPs encapsulating elastogenic factors, such as TGF-β1 or hyaluronan oligomers (HA-o) which have shown promise in vitro in elastogenic induction of aneurysmal SMCs could be included. See Sylvester et al., Acta Biomater. 9(12):9292-302 (2013) and Venkataraman et al., J Tissue Eng Regen Med. April 16. doi: 10.1002/term.1889 (2014), which show that TGF-β and HA-o can be released from PLGA using NPs that were surface functionalized with PVA, which imparts negative surface charge.

In the method of dissolving a blood clot, the fibrinolytic nanoparticles are administered to a subject. Generally speaking, the fibrinolytic nanoparticles are administered intravenously. However, in some embodiments, the fibrinolytic nanoparticle may also be administered orally, intramuscularly, intradermally, intraperitoneally, intralymphaticly, percutaneously, or by scarification, subcutaneous injection or other parenteral routes.

In each of the above embodiments, a nanoparticle of the invention maybe combined with a pharmaceutically acceptable vehicle or carrier to provide a pharmaceutical composition. The fibrinolytic nanoparticles may be present in a pharmaceutical composition in an amount from 0.001 to 99.9 wt %, more preferably from about 0.01 to 99 wt %, and even more preferably from 0.1 to 95 wt %. For instance, in embodiments where these fibrinolytic nanoparticles are administration by injection (e.g., intraperitoneally, intravenously, subcutaneously, intramuscularly, etc.), the compositions are preferably combined with pharmaceutically acceptable vehicles such as saline, Ringer's solution, dextrose solution, and the like.

In another embodiment of this invention, the NPs maybe modified/combined with suitable agents for enhancing their delivery and targeting efficiency, as well as their uptake and retention, tracking and/or diagnostic capabilities. Targeting may be enhanced by agents such as but not limited to antibodies targeting fibrin, platelets/platelet receptors, as well as components of the extracellular matrix, or products thereof. Additionally, the use of agents such as super paramagnetic iron-oxide particles (SPIO micro/nanoparticles) can also serve to enhance the targeting specificity of the fibrinolytic NPs developed by the inventors.

The compositions for administration will commonly comprise a suspension of the fibrinolytic nanoparticles in a pharmaceutically acceptable carrier, preferably an aqueous carrier, which is selected so as not to affect the biological activity of the combination. Examples of such carriers are distilled water, physiological phosphate-buffered saline, Ringer's solutions, dextrose solution, and Hank's solution. These suspensions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Single or multiple administrations of the compositions may be administered depending on the dosage and frequency as required and tolerated by the subject. In any event, the administration regime should provide a sufficient quantity of the composition of this invention to effectively treat the subject. The formulated fibrinolytic nanoparticles can be administered as a single dose or in multiple doses.

One of skill in the art will recognize that the amount of the fibrinolytic nanoparticles in these formulations can vary widely, and will be selected primarily based on fluid volumes, viscosities, body weight and the like in accordance with the particular mode of administration selected and the subject's needs. In one embodiment, the amount of fibrinolytic nanoparticle administered is between about 0.25 µmol/kg and about 3 µmol/kg. In another embodiment, the amount of fibrinolytic nanoparticle administered is between about 0.5 µmol/kg and about 1.5 µmol/kg. In yet another embodiment, the amount of fibrinolytic nanoparticle administered is about 1 µmol/kg. In still another embodiment, the amount of nanoparticle administered is between about 0.3 g/kg and about 0.4 g/kg.

The following example is included for purposes of illustration and is not intended to limit the scope of the invention.

EXAMPLE

Example: Nanotherapeutics for Controlled Fibrinolysis in Abdominal Aortic Aneurysms Abdominal aortic aneurysms (AAAs) involve chronic overexpression of inflammatory cells and proteases that disrupt elastic matrix within the abdominal aorta wall, leading to a progressive loss of vessel elasticity. Approximately 75% of all AAAs contain an intraluminal thrombus (ILT), which has been variably described as a) a bioinert mechanical barrier, protecting the underlying AAA wall from high hemodynamic stresses, b) a reservoir of inflammatory cells and proteases that contributes to matrix breakdown in the AAA wall, and c) a barrier to the transport of nutrients and therapeutics from blood into the AAA wall. In consideration of these aspects, revascularization of AAAs mandates slow, incomplete thrombolysis to render the ILT porous for transmural diffusion of therapeutics from circulation while avoiding bulk release of inflammatory cells and proteases that can accelerate matrix breakdown in the AAA wall, and while continuing to mechanically bolster the weakened AAA wall. Tissue plasminogen activator (tPA) a thrombolytic agent, has previously been used to rapidly revascularize vessels in acute stroke and myocardial infarctions. The inventors have sought to investigate the ability of tPA delivered slowly from poly(lactic-co-glycolic acid) nanoparticles (PLGA NPs) to gradually lyse fibrin clots without any adverse pro-proteolytic and anti-matrix regenerative effects on aneurysmal smooth muscle cells (SMCs) They have shown that cationic surface functionalization of NPs enables their enhanced binding to the clot relative to anionic PLGA NPs, due to electrostatic interactions with negatively-charged fibrin, and that this mode of delivery enables more regulated tPA release and more gradual clot lysis versus exogenous tPA. Plasmin released following clot lysis via NPs was found to prevent net increases in elastic matrix deposition by cultured rat aneurysmal SMCs (EaR-ASMC). The data indicates that the lack of increases in elastic matrix are not due to increases in activity of elastolytic matrix metalloproteases (MMPs) 2 and 9 in EaR-ASMC cultures, which were in fact attenuated, but rather due to increased generation of plasmin, which has known proteolytic activity. These are the first studies evaluating modalities for gradual clot lysis for specific application to revascularizing AAA segments and facilitating transmural delivery of endolumenally delivered AAA therapeutics Materials and Methods Formulation of PLGA NPs. NPs were formulated from poly (dl-lactic-co-glycolic acid) (PLGA; 50:50 lactide: glycolide; inherent viscosity 0.95-1.20 dL/g in hexafluoroisopropanol; Durect Corporation, Birmingham, Ala.). A double emulsion-solvent evaporation technique was utilized to encapsulate tissue plasminogen activator (tPA, human; Calbiochem, San Diego, Calif.), as described (for other therapeutic agents) in recent studies by the inventors. (Sivaraman B, Ramamurthi A., Acta Biomater. 9:6511-25 (2013); Sylvester et al., Acta Biomater., 9:9292-302 (2013)). Briefly, 50 mg of PLGA was dissolved in 2.0 mL of either chloroform (Fisher Scientific, Fair Lawn, N.J.) or dichloromethane (Sigma-Aldrich, St. Louis, Mo.), depending on the emulsion stabilizer used during the formulation(s). Chloroform was used as the organic solvent for NP formulation with didodecyldimethylammonium bromide (DMAB; Sigma-Aldrich) as the stabilizer, while dichloromethane was used as the solvent for NPs formulated using poly(vinyl alcohol) (PVA; Sigma-Aldrich) as the stabilizer.

tPA (10 µg in 100 µL of nanopure water) was emulsified into the PLGA solution using a probe sonicator (Q500; QSonica LLC, Newtown, Conn.) to form a water-in-oil emulsion. This primary emulsion was then emulsified into an aqueous solution of 0.25% w/v DMAB or PVA to form a water-in-oil-in-water emulsion. All sonication steps were carried out on ice for 1 min, at a 20% amplitude setting. The NP suspension thus formulated was stirred for 16 h at room temperature, and then desiccated for 1 h under vacuum, to remove traces of the organic solvent(s). NPs were recovered by ultracentrifugation at 35,000 rpm (Beckman L-80, Beckman Instruments, Inc., Palo Alto, Calif.). The NPs were further washed twice with nanopure water, sonicated and ultracentrifuged (30,000 rpm) to remove residual stabilizer and unencapsulated tPA, and then lyophilized for 48 h to obtain a dry powder.

Size and surface charge measurements on tPA-loaded PLGA NPs. The mean hydrodynamic diameter of the NPs were determined using a dynamic light scattering technique, and their mean zeta potential (i.e., surface charge) were determined via a phase analysis light scattering technique using a commercial particle-sizing system (PSS/NICOMP 380/ZLS, Particle Sizing Systems, Santa Barbara, Calif.), as previously described by the inventors.

Efficiency of tPA encapsulation and tPA release from NPs. In order to determine the efficiency of encapsulating tPA within the PLGA NPs for subsequent release, tPA was conjugated with Alexa Fluor® 633 (AF633; carboxylic acid, succinimidyl ester; Life Technologies, Carlsbad, Calif.), as per a protocol adapted from the company. Briefly, a 0.1 mL aliquot of AF633 (containing 500 µg of dye) was added to 0.1 mL of tPA solution (containing 10 µg tPA) and allowed to undergo bioconjugation with gentle shaking, on a shaker for 1 h. Unconjugated AF633 was removed by dialysis (10 kDa molecular weight cutoff; Spectrum Laboratories, Rancho Dominguez, Calif.) against phosphate buffered saline (PBS; Sigma-Aldrich) for 24 h, with PBS being replaced every 8 h. AF633-conjugated tPA (f-tPA) was then encapsulated as described in Section 2.1, at a loading of 10 µg. The supernatants from the washing/ultracentrifugation steps were pooled for each individual NP formulation. The unencapsulated f-tPA was quantified fluorometrically (excitation $\lambda=580$ nm, emission $\lambda=650$ nm) using a SpectraMax M2 plate reader (Molecular Devices, Inc., Sunnyvale, Calif.), based on a standard calibration curve generated with serial dilutions of a known concentration of f-tPA. The secondary excitation peak for AF633 at $\lambda=580$ nm was used (instead of the primary peak at 633 nm), to avoid interference by the significant fluorescence due to PBS at 633 nm.

Release of f-tPA from the NPs was also assessed using fluorometry (excitation $\lambda=580$ nm, emission $\lambda=650$ nm), as described above. Briefly, 1.5 ml polypropylene microcentrifuge tubes (n=6 per formulation) were filled with 1.0 mL of a 3.0 mg/mL suspension (in PBS; pH 7.4) of the DMAB- and PVA-functionalized fibrinolytic NPs (referred to as DMAB-FNPs and PVA-FNPs in the manuscript henceforth), and incubated at 37° C. on a shaker at 100 rpm. Based on initial testing, this NP concentration was used in order to be able to detect f-tPA release levels in the ng/mL range. Release was carried out over 48 h, with sampling of the f-tPA at specific time points (10, 20, 30, 45, 60 and 120 min over the first 2 h, followed by 24 h and 48 h). At each analysis time point, the samples were centrifuged (14,000 rpm, 5 min, 4° C.) in a microcentrifuge (Beckman Microfuge 16®, Beckman Coulter, Inc.), the supernatants were withdrawn to quantify the f-tPA content and the volume was replenished with fresh PBS. The f-tPA released was quantified fluorometrically (SpectraMax M2, Molecular Devices, Inc.), based on a standard calibration curve constructed using serial dilutions of a known concentration of f-tPA. Since previous studies encapsulating tPA within PLGA-based NPs showed the majority of tPA release to occur over the initial 120 min, 2 sets of NP suspensions (from the same batch formulated) were utilized for both DMAB and PVA-NPs, in order to accurately obtain data for release over this initial period. (Chung et al., Biomaterials, 29:228-37 (2008). Wang et al., J Biomed Mater Res.; 91A:753-61 (2009)).

Figure 4:
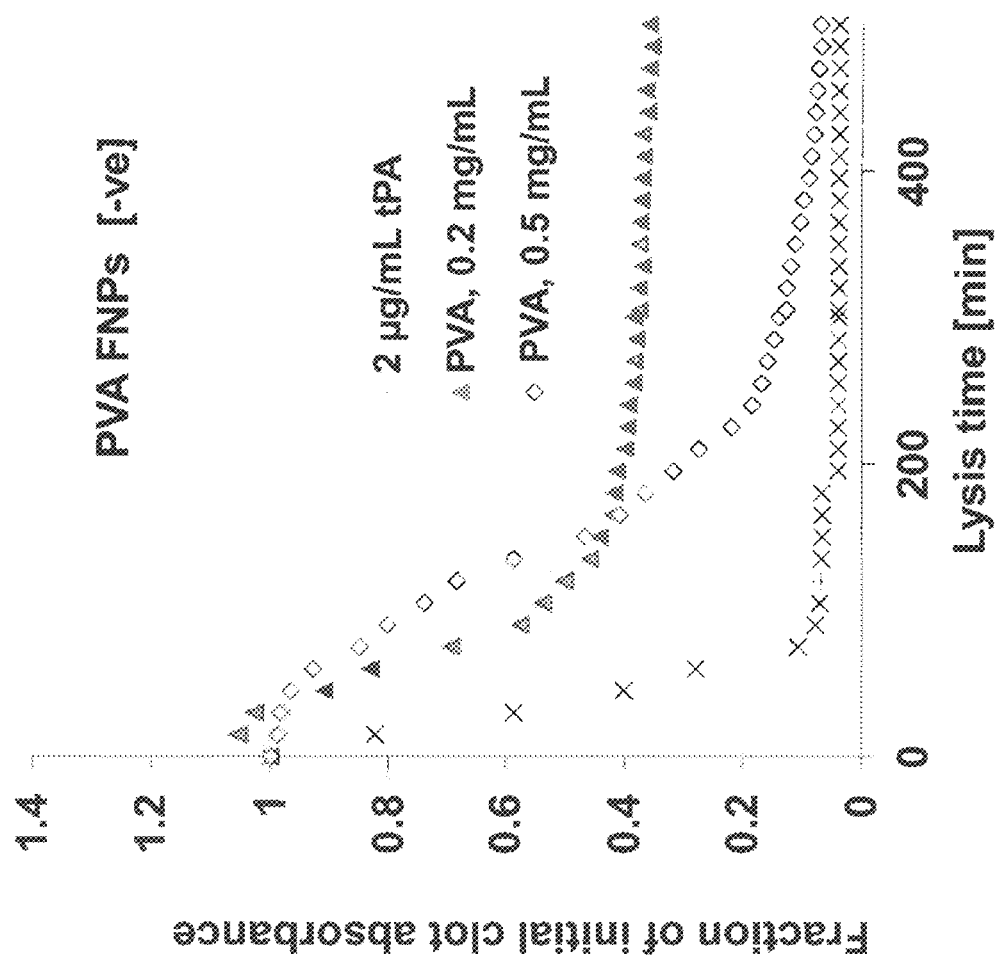
FIG. 4 provides a graph showing the in vitro clot lysis profiles of fibrinolytic PVA-functionalized NPs loaded with 50 µg of tPA at 0.2 and 0.5 mg/mL NP concentrations, with 2 µg/mL of tPA solution as the exogenous control. The absorbance of the NP-lysed clot (at 405 nm), calculated by subtracting the absorbances of control wells (containing only NPs) from that of wells containing the NPs with clot, was plotted as a fraction of its initial absorbance as a function of time. All values plotted are mean values of three different clots.
Figure 5:
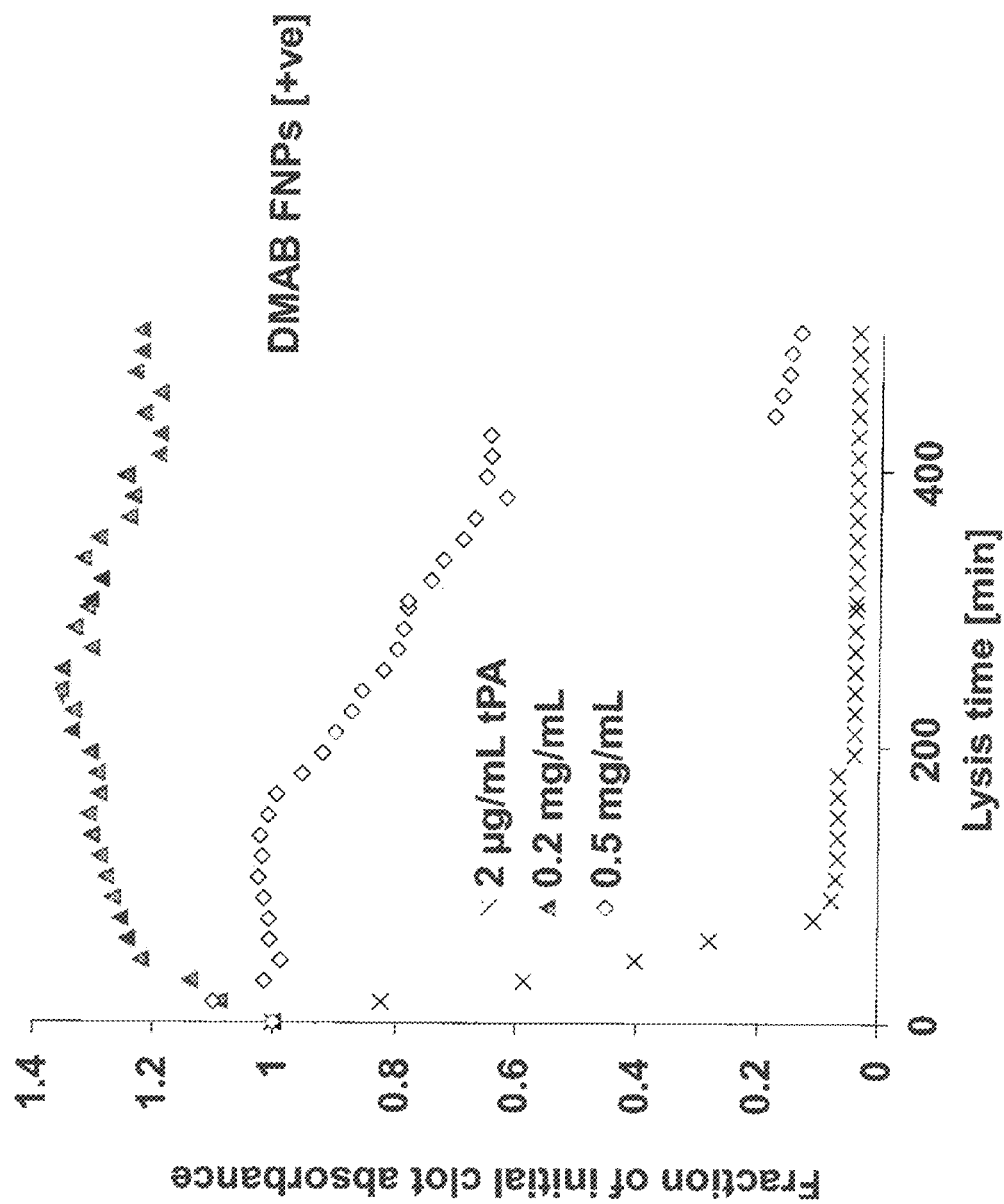
FIG. 5 provides a graph showing the in vitro clot lysis profiles of fibrinolytic DMAB-functionalized NPs loaded with 50 µg of tPA at 0.2 and 0.5 mg/mL NP concentrations, with 2 µg/mL of tPA solution as the exogenous control. The absorbance of the NP-lysed clot (at 405 nm), calculated by subtracting the absorbances of control wells (containing only NPs) from that of wells containing the NPs with clot, was plotted as a fraction of its initial absorbance as a function of time. All values plotted are mean values of three different clots.

In vitro fibrinolysis by NPs. Initial experiments were carried out to see whether tPA delivered from NPs would indeed be able to lyse a fibrin clot, and also, how quickly this would occur compared to an exogenous dose of 2 ug/mL tPA. The results of these experiments are shown in FIGS. 4 and 5. A preliminary fibrinolysis experiment was first carried out with PVA- and DMAB-FNPs encapsulating 50 µg tPA, to evaluate their ability to lyse fibrin clots, and compare it with the effects of an exogenous tPA control (2.0 µg/mL tPA solution). Based on the results from this initial clot lysis experiment that showed clot lysis by the NPs was prolonged relative to clot lysis by exogenous tPA, the inventors subsequently sought to further extend fibrinolysis by loading PVA- and DMAB-NPs with only 10 µg of tPA. To match the steady-state level of tPA released from the PVA-NPs at ~48 h (FIG. 6), an equivalent dose (0.2 µg/mL) of exogenous tPA was tested. Note that the normal IV dose of tPA is between 1-1.5 mg/kg in humans, which translates to around 14-17.5 µg/mL.

The fibrinolytic efficacy of the tPA-loaded NPs was examined in a 96-well plate, as described in studies by other groups, by monitoring the decrease in absorbance of the fibrin clot (as a ratio to its initial absorbance prior to addition of FNPs) at a wavelength of 405 nm as a function of time. (Cellai et al., Clin Appl Thromb Hemost, 16:337-44 (2010)). The fibrin clot in each well was formed by mixing human fibrinogen (0.1 mL of 3.0 mg/mL solution; FIB 1; Enzyme Research Laboratories, South Bend, Ind.), human plasminogen (6 µL of 1.0 mg/mL solution; Calbiochem) and human thrombin (0.1 mL of 1.0 U/mL solution; Calbiochem), in 40 mM Tris/HCl buffer (Sigma-Aldrich) containing 75 mM NaCl (Sigma-Aldrich). Clot formation was allowed to progress for 1 h at 24° C. The absorbance ($\lambda$=405 nm) of the clot was measured at 1 min intervals over this time, and was found to plateau thereafter. Following this, the fibrinolytic PLGA NPs (50 µL) were added to the clot at concentrations of 0.1, 0.2 and 0.5 mg/mL, with a similar volume of tPA and Tris/HCl buffer added as the exogenous and clot controls, respectively. The absorbances of the clot at different time points were calculated by subtracting the absorbances of control wells containing only NPs from that of wells containing the clot with FNPs as it lysed the clot.

Impact of surface charge of NPs on their clot binding affinity. PLGA NPs encapsulating AF633 were formulated using a protocol similar to that described earlier with PVA and DMAB as the stabilizers. To compare their clot binding affinities, NPs (50 µL) were added to fibrin clots (formed as described herein) in a 96-well plate at three different NP concentrations (0.1, 0.2 and 0.5 mg of NPs; n=6 per NP type) and incubated with the clots for 60 min. To assess non-specific binding of NPs to the wells (if any), empty wells were also incubated with NPs at the three concentrations mentioned. At the end of the incubation step, the supernatant solution was collected, and all wells (elastin and empty blanks) were washed with PBS, with the wash solutions being collected and added to the supernatant for fluorometric analysis for NP content. The dilution of the supernatant due to the addition of solution from the wash steps was taken into account in the subsequent quantification of NP binding.

Clot binding efficacy of the NPs was estimated from the decrease in fluorescence of the supernatant $\lambda_{excitation}$=580 nm, $\lambda_{emission}$=650 nm) based on a calibration curve prepared from \ serial dilutions of suspensions containing known concentrations of the different NPs. The total NP binding to the clots was obtained by subtracting the amount of NPs adherent to the empty wells from the amount adherent in the wells containing the clot, and is expressed as a percentage of the amount added.

Isolation and culture of SMCs from elastase perfusion-induced rat AAAs. Aneurysmal rat aortic SMCs (EaRASMCs) were isolated from adult male Sprague-Dawley rats (n=3) at 14-days post-AAA induction via elastase infusion, as described in an earlier study by our group [8]. Briefly, the aneurysmal aortae were excised, cut open longitudinally, and the intimal layer was scraped off gently. The media layer was carefully dissected from the underlying adventitia, chopped into 0.5 mm pieces, and washed with fresh, warm, sterile PBS. The tissues were pooled and digested in DMEM-F12 cell culture medium (Invitrogen) containing collagenase (125 U/mg; Worthington Biochemicals, Lakewood, N.J.) and elastase (3 U/mg; Worthington Biochemicals) for 30 min at 37° C., centrifuged (400 g, 5 min), and cultured over 14 days in T-75 flasks. The cells were cultured in DMEM-F12 medium supplemented with 10% v/v fetal bovine serum (FBS; Invitrogen) and 1% v/v PenStrep (Thermo Fisher, South Logan, Utah). The primary EaRASMCs obtained from these tissue explants were expanded over 2 weeks, and passaged upon attaining confluence.

Experimental design for cell culture. All cell culture experiments for evaluating the effects of tPA release from the NPs and subsequent fibrinolysis on EaRASMC proliferation, elastic matrix preservation, MMP production & activity, and plasmin activity were carried out in a transwell assay system. This comprised EaRASMCs in the well plate, with the fibrin clot and NPs within a transwell insert. EaRASMCs (passages 2-5) were seeded at $3\times10^4$ cells/well and cultured over a total of 21 days in 6-well plates (A=10 $cm^2$; USA Scientific, Ocala, Fla.) in DMEM-F12 supplemented with 10% v/v FBS and 1% v/v PenStrep. Following seeding, the EaRASMCs were allowed to proliferate for 10 days, to allow them to deposit measurable amounts of elastic matrix. On day 10 post-cell seeding, the fibrin clot was formed for 1 h (as described above in Section 2.4) in a 6-well cell culture insert (ThinCert™, Greiner Bio-One, Monroe, N.C.). DMAB- and PVA-FNPs (encapsulating 10 µg tPA) were added to the clot at a concentration of 0.5 mg/mL, and the transwell assay system now comprising the clot and NPs in the insert and EaRASMCs in the wells of the 6-well plate was cultured for a further 11 days. EaRASMCs without clots served as the cell control, while those cultured with a clot served as the clot control. Additional controls for the experimental sets to be analyzed for elastic matrix deposition included EaRASMC layers cultured with 0.2 µg/ml of exogenous tPA for 11 days, following an initial 10 days of culture without tPA. The cell layers were harvested after 21 days of culture. It must be noted that for immunofluorescence detection of elastic matrix proteins, cells were cultured on 42 mm×42 mm glass cover slips (VWR Scientific) within the 6-well plate.

DNA assay for cell proliferation. A fluorometric assay (Labarca C, Paigen K., Anal Biochem, 102: 344-52 (1980)) using the Hoechst 33258 dye (Invitrogen) was utilized to determine the DNA content of the cell layers, towards assessing the effects of tPA released and fibrinolytic products on EaRASMC proliferation. The cell layers were harvested at 1 day and 21 days of culture in NaCl-Pi buffer, sonicated on ice and assayed for DNA content. The cell density was calculated, assuming 6 pg DNA per cell.

Fastin assay for elastin. The total elastin content in the harvested EaRASMC cell layers was quantified using a Fastin assay (Accurate Scientific and Chemical, Westbury, N.Y.), as described in recent publications by the inventors. (Sivaraman B, Ramamurthi A., Acta Biomater. 9:6511-25 (2013); Sylvester et al., Acta Biomater., 9:9292-302 (2013)). Cell layers harvested in NaCl-Pi buffer, were sonicated on ice to homogenize the cell layer. Following this, the cell layer suspension was digested with oxalic acid, as per the manufacturer's protocol, to extract elastin. Briefly, a 300 µL aliquot of the cell layer suspension was first mixed with 100 µL of 1.0 M oxalic acid and digested (90 min, 95° C.), centrifuged at 14,000 rpm, and the supernatant (containing solubilized elastin) extracted. 400 µL of 0.25 M oxalic acid was then added to the remainder of the cell layer, and further digested for 60 min at 95° C. The extracts from the two digestion steps were pooled, and the elastin content within these cell layers was assayed using the Fastin assay. The amounts of elastin measured were also normalized to their corresponding DNA amounts, so as to provide an accurate comparison between the different treatments.

Western blots for MMP-2 and MMP-9 protein synthesis. The impact of the tPA released from NPs and the fibrinolytic products following clot lysis on MMP-2 and -9 synthesis by EaRASMCs was semi-quantitatively assessed by western blot analysis, as previously described. After 21 days of culture, the cell layers were harvested in RIPA buffer (Thermo Scientific) containing Halt™ protease inhibitor (Thermo Scientific), and assayed for total protein content using a bicinchonic acid (BCA) assay kit (Thermo Scientific). Maximum volumes of sample protein (15.6 µL) were then loaded under reduced conditions into each lane of a 10% sodium dodecylsulfate-polyacrylamide gel electrophoresis (SDS-PAGE) gel (Invitrogen), along with a SeeBlue® pre-stained molecular weight ladder (Invitrogen). Following the electrophoresis step, the gels were transferred onto nitrocellulose membranes (iBlot® Western Blotting System, Invitrogen). The membranes were blocked with Odyssey Blocking Buffer (LI-COR Biosciences, Lincoln, Nebr.) for 1 h at room temperature, following which they were immunolabeled for 16 h at 4° C. with a rabbit polyclonal antibody against MMP-2 (1:500 dilution; Abcam, Cambridge, Mass.) or a rabbit monoclonal antibody against MMP-9 (1:500 dilution; Millipore, Inc.), with a mouse monoclonal antibody against β-actin (1:1000 dilution; Sigma-Aldrich) as the loading control. Secondary antibody labeling was carried out for 1 h at room temperature using IRDye® 680LT goat-anti-rabbit (1:15,000 dilution) and IRDye® 800CW goat-anti-mouse (1:20,000 dilution) polyclonal antibodies (LI-COR Biosciences). Fluoroluminescence detection of the protein bands was then carried out using a LI-COR Odyssey laser-based scanning system. The intensities of MMP-2 bands on all gels were quantified using ImageJ software, expressed in terms of relative density units (RDU) and normalized to the intensity of their respective β-actin bands to enable comparison between the different test cases within the same blot. The normalized band intensities of active MMP-2 for the PLGA NP-treated and NP-untreated EaR-ASMC cell control cultures were further normalized to those of the NP-untreated clot control cultures to determine the fold-change(s) in production of active MMP-2, and the statistical significance of the differences between them. The results presented in this manuscript were averaged from 3 replicate gels run per culture treatment.

Gel zymography for MMP-2 and MMP-9 activity. The effects of tPA released from NPs and of the products of fibrinolysis on MMP-2 and -9 activities in EaRASMC cell layers were analyzed via gel zymography. Briefly, volumes of the cell layer samples (harvested in RIPA buffer containing protease inhibitor) equivalent to 10 µg of protein, were loaded into each lane of a 10% zymogram gel (Invitrogen), along with a SeeBlue® pre-stained molecular weight ladder (Invitrogen). The gel was run for 2 h at 125 V. The gels were then washed in a buffer containing 2.5% v/v Triton-X-100 for 30 min to remove SDS, and then incubated for 48 h in a substrate/development buffer to activate the MMPs. The gels were stained with Coomassie Brilliant Blue solution for 45 min, and destained for 90 min, until clear bands appeared visible against the blue background of the gel. Band intensities (RDU) of the bands obtained for test cultures were quantified using ImageJ software, and normalized to those obtained for the NP-untreated control cultures to determine fold changes in MMP-2 and -9 activities. Data was acquired from 3 independent replicate gels.

Plasmin activity within EaRASMC cell layers. The chromogenic plasmin synthetic substrate S2403 (Diapharma, Inc., West Chester, Ohio) was utilized to measure plasmin activity in EaRASMC layers. Volumes of cell layer samples (harvested in RIPA buffer containing protease inhibitor) equivalent to 20 µg of protein were incubated with S2403 (final concentration=0.3 mM) [48] for 24 h at 24° C. A calibration curve was constructed based on the absorbances of serial dilutions of plasmin incubated similarly with S2403. Plasmin activity within the cell layers was calculated from the absorbance of the cell layer samples at $\lambda=405$ nm, based on the plasmin calibration curve, and expressed in terms of ng of plasmin per 20 µg of protein in the cell layer.

Immunofluorescence-based visualization of elastic matrix proteins in cell layer. For immunofluorescence studies, EaRASMCs were seeded and cultured on glass cover slips, with a fibrin clot being formed within a 6-well cell culture insert, and lysed with PVA- and DMAB-FNPs beginning 10 days after EaRASMC seeding. After a total of 21 days of culture of the EaRASMCs, the cell layers were fixed with ice-cold methanol and treated with a rabbit anti-rat polyclonal antibody against elastin (Millipore) at 1:100 v/v dilution. The detected proteins were visualized with Alexa633-conjugated IgG secondary antibodies (1:1000 v/v dilution; Invitrogen). The cell layers were mounted with Vectashield containing DAPI (Vector Laboratories, Burlingame, Calif.) which labels the cell nuclei. A minimum of 6 regions per cell layer from a total of n=3 replicate treatments were imaged to assess representative outcomes. Imaging was carried via confocal microscopy (Leica TCS SP5 II, Leica Microsystems, Inc.).

Statistical analysis. All experimental data presented (n=6/condition, unless stated otherwise) represent mean values with standard deviation (SD). Statistical significance of differences between mean values for different samples and conditions was evaluated using a Student's t-test, with $p \leq 0.05$ considered as statistically significant.

Results

Formulation and characterization of tPA-loaded PLGA NPs. The NPs formulated with both PVA and DMAB exhibited mean hydrodynamic diameters of 358±5 nm and 446±20 nm, respectively. The surface charges (ξ-potentials) of the NPs were −36±2 mV and +23±3 mV for PVA-FNPs and DMAB-FNPs, respectively. As observed in Table 1, incorporation of tPA (or f-tPA; data not shown) did not affect the size or charge of the NPs significantly.

Encapsulation and release of tPA from PLGA NPs. The supernatant solutions generated during the centrifugal pelletting of the formulated NPs contained less than 5 ng/mL of f-tPA, which based on the calibration curve of serial dilutions of f-tPA, suggests that ≥90% of f-tPA was encapsulated within the NPs.

TABLE 1

Size and surface charge of PLGA NPs encapsulating tPA, formulated with PVA and DMAB as the emulsion stabilizers (n = 6 replicate formulations, mean ± 95% CI).

| Sample | Size (nm) | Zeta Potential (mV) |
|---|---|---|
| PVA - 0 µg tPA | 358 ± 5 | −36 ± 2 |
| PVA - 10 µg tPA | 344 ± 16 | −33 ± 2 |
| DMAB - 0 µg tPA | 446 ± 20 | +23 ± 3 |
| DMAB - 10 µg tPA | 476 ± 9 | +21 ± 1 |

Figure 6:
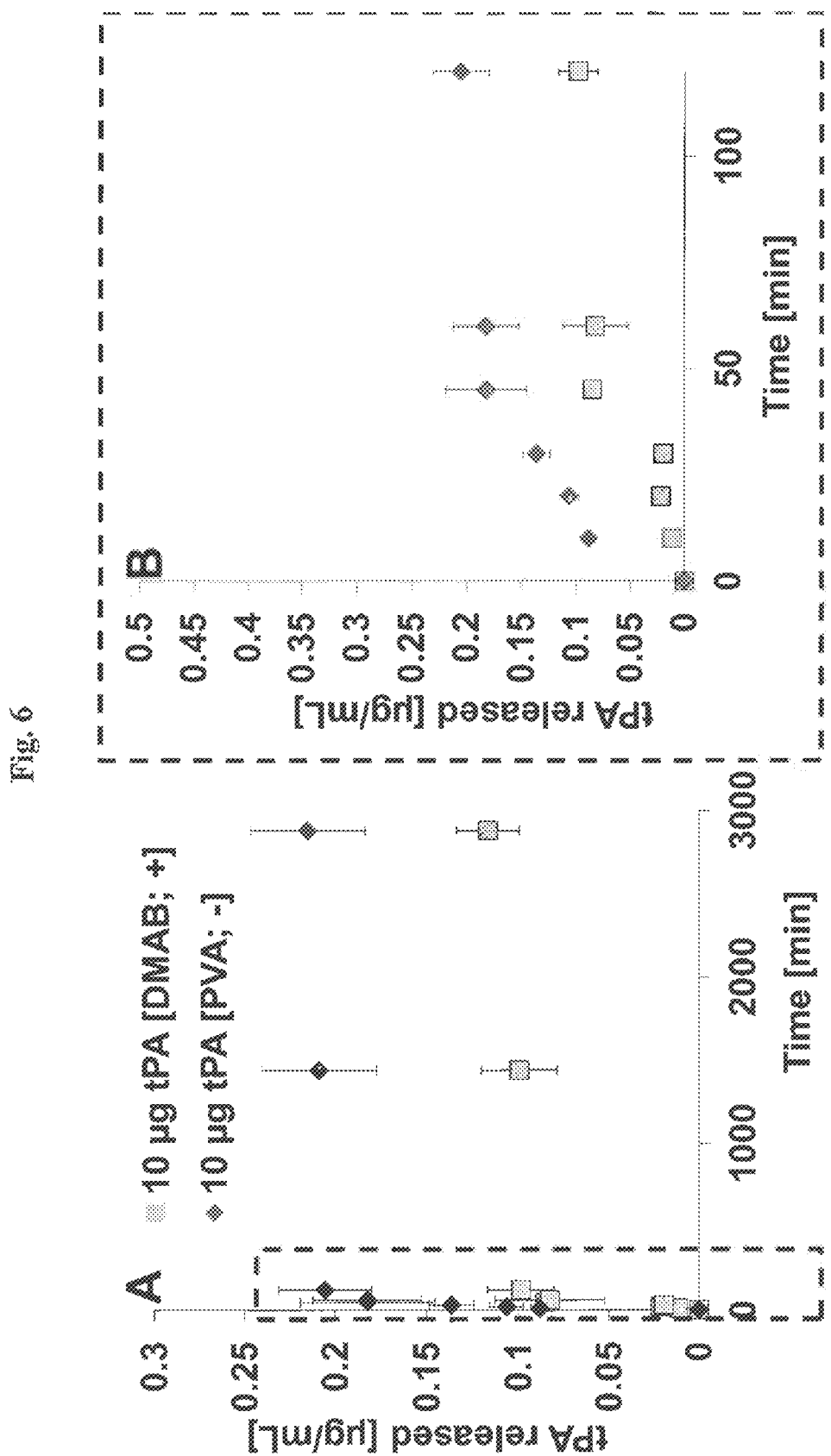
FIG. 6 provides a graph showing the (A) in vitro release profiles for tissue plasminogen activator (tPA) from the PLGA NPs (10 µg of tPA loading) functionalized with PVA and DMAB, at a NP concentrations of 3.0 mg/mL (n=6 per group; mean±SD) (B) Inset of the release profile for tPA over the initial 2 h of release.

The cumulative release of f-tPA from NPs (10 mg/mL NP concentration) is shown in FIG. 6. Significant release of tPA occurred during the initial 2 h, following which a release plateau was attained by ~48 h. Also, the steady-state f-tPA concentration (0.1 µg/mL) generated by DMAB-FNPs was significantly lower ($p<0.05$) than that generated by PVA-FNPs (0.2 µg/mL).

Fibrinolytic efficacy of tPA-loaded PLGA NPs. Preliminary experiments utilizing PLGA NPs encapsulating 50 µg of tPA showed them to successfully lyse fibrin clots in vitro. Clot lysis time, as defined as the duration for the clot absorbance to decrease to 50% of its initial value, was longer for tPA released from the NPs, compared to exogenous tPA (2 µg/mL). PVA-FNPs demonstrated more rapid fibrinolysis compared to DMAB-FNPs, with the former exhibiting lysis times between 105 min (for 0.2 mg/mL NP concentration) and 145 min (for 0.5 mg/mL NP concentration). DMAB-FNPs, on the other hand, exhibited clot lysis times of 960 min (for 0.2 mg/mL NP concentration) and 420 min (for 0.5 mg/mL NP concentration).

Towards achieving more controlled/gradual clot lysis, the fibrinolytic efficacy of NPs encapsulating lower amounts (10 µg) of tPA was evaluated. The exogenous control (0.2 µg/mL tPA solution) showed a clot lysis time of ~20 min. Differently, as seen in FIG. 7A, the absorbance of fibrin clots treated with 0.5 and 1.0 mg/mL PVA-FNPs decreased to approximately 36% of its initial value after 5 h, and that of clots incubated with 0.2 mg/mL NPs was ~89% of the initial clot absorbance after the same duration. However, at the 24 h time-point, the absorbance of the clots treated with 0.2 mg/mL NPs decreased significantly to 55% of its initial value, while those of clots incubated with 0.5 and 1.0 mg/mL NPs decreased further only marginally to 26% and 30% of their initial value. Due to the discrete sampling events being spread over the entire extended period of lysis, the inventors could not accurately identify the exact time point at which the absorbance of the clot decreased to 50% of its initial value, but based on the data, they estimated that the clot lysis time for 0.2 mg/mL of PVA-NPs is longer than 24 h, while that for 0.5 and 1.0 mg/mL of PVA NPs lies between 5-24 h.

Fibrinolysis was even slower for DMAB-FNPs loaded with 10 µg tPA, with the absorbances of clot treated with 0.2, 0.5 and 1.0 mg/mL NP concentrations decreasing marginally to ~88% of their initial value after 5 h. However, even after 24 h of incubation with the clot, only the DMAB-FNPs at a concentration of 0.5 mg/mL decreased clot absorbance below 50% of its initial value (36%), while those at 0.2 and 1.0 mg/mL NP concentrations showed moderate decreases to 67 and 70% of their initial values. The inventors therefore estimate that the clot lysis time for 0.5 mg/mL of DMAB-FNPs lies between 5-24 h, while that for 0.2 and 1.0 mg/mL of DMAB-FNPs is longer than 24 h. Overall, lower tPA encapsulation within the NPs cause more gradual lysis of fibrin clots, with the DMAB-FNPs exhibiting more gradual lysis profiles compared to the PVA-FNPs.

Figure 8:
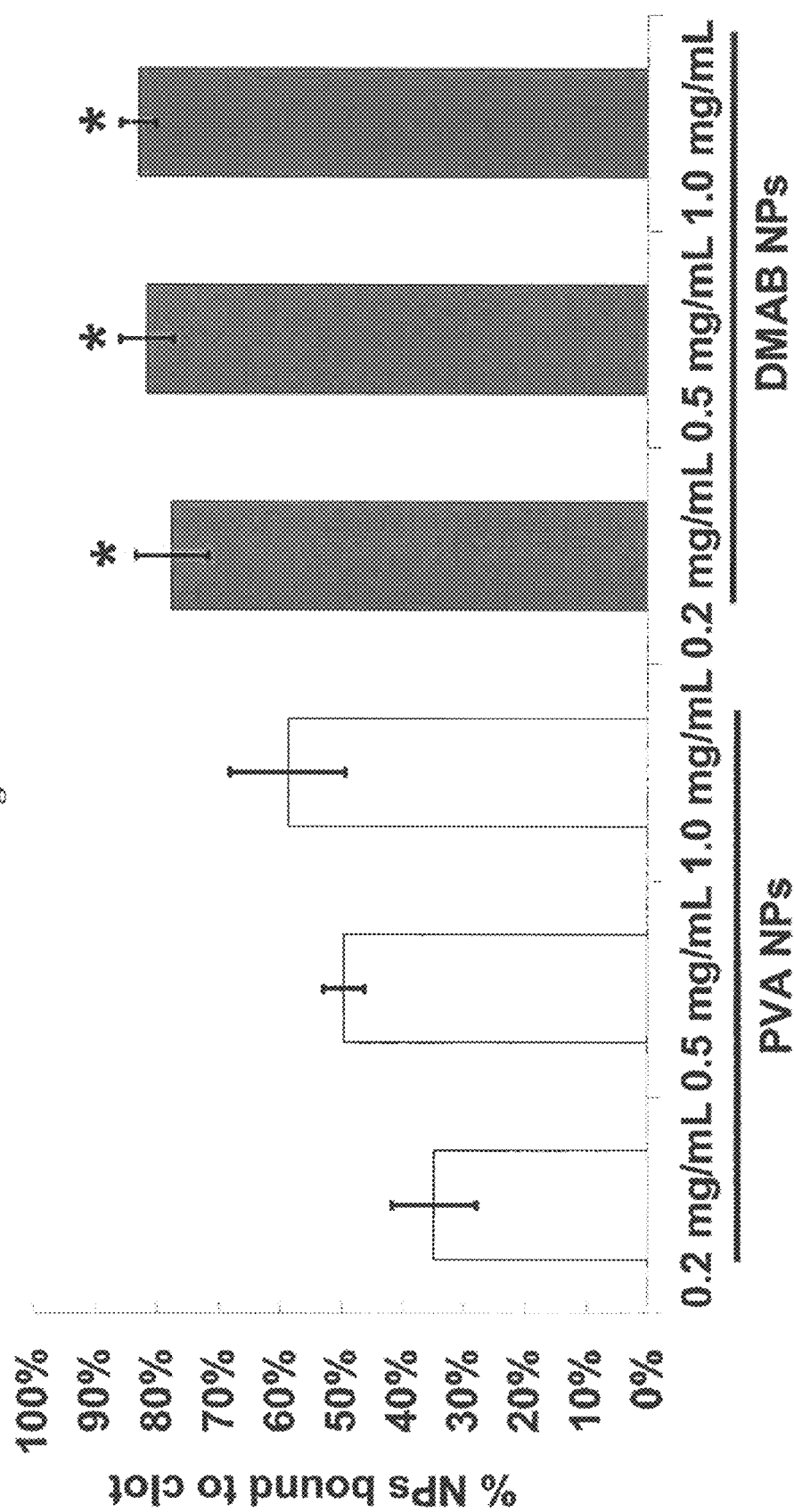
FIG. 8 provides a graph showing the percentage of PLGA NPs functionalized with PVA and DMAB (with AF633 encapsulated within) bound to fibrin clots. (mean±SD; n=6/case, * denotes p<0.05 compared to corresponding amount of PVA-functionalized PLGA NPs) Note: The percentage retention was calculated after subtracting the amount of NPs adhering to empty wells.

Effects of surface charge of FNPs on their clot binding affinities. NPs encapsulating AF633 were utilized to quantify the binding efficiency of DMAB- and PVA-surface functionalized NPs to fibrin clots. As shown in FIG. 8, the DMAB-functionalized NPs exhibited a greater binding to the fibrin clots, compared to the PVA-functionalized NPs. For DMAB-NPs, 77.6±2.9%, 81.7±4.2% and 83.2±5.9% of NPs bound to the fibrin clot at NP concentrations of 0.2, 0.5 and 1.0 mg/mL, respectively; the corresponding figures for PVA-NPs, were 34.8±9.4%, 49.6±3.4% and 58.9±7.0% respectively.

Figure 9:
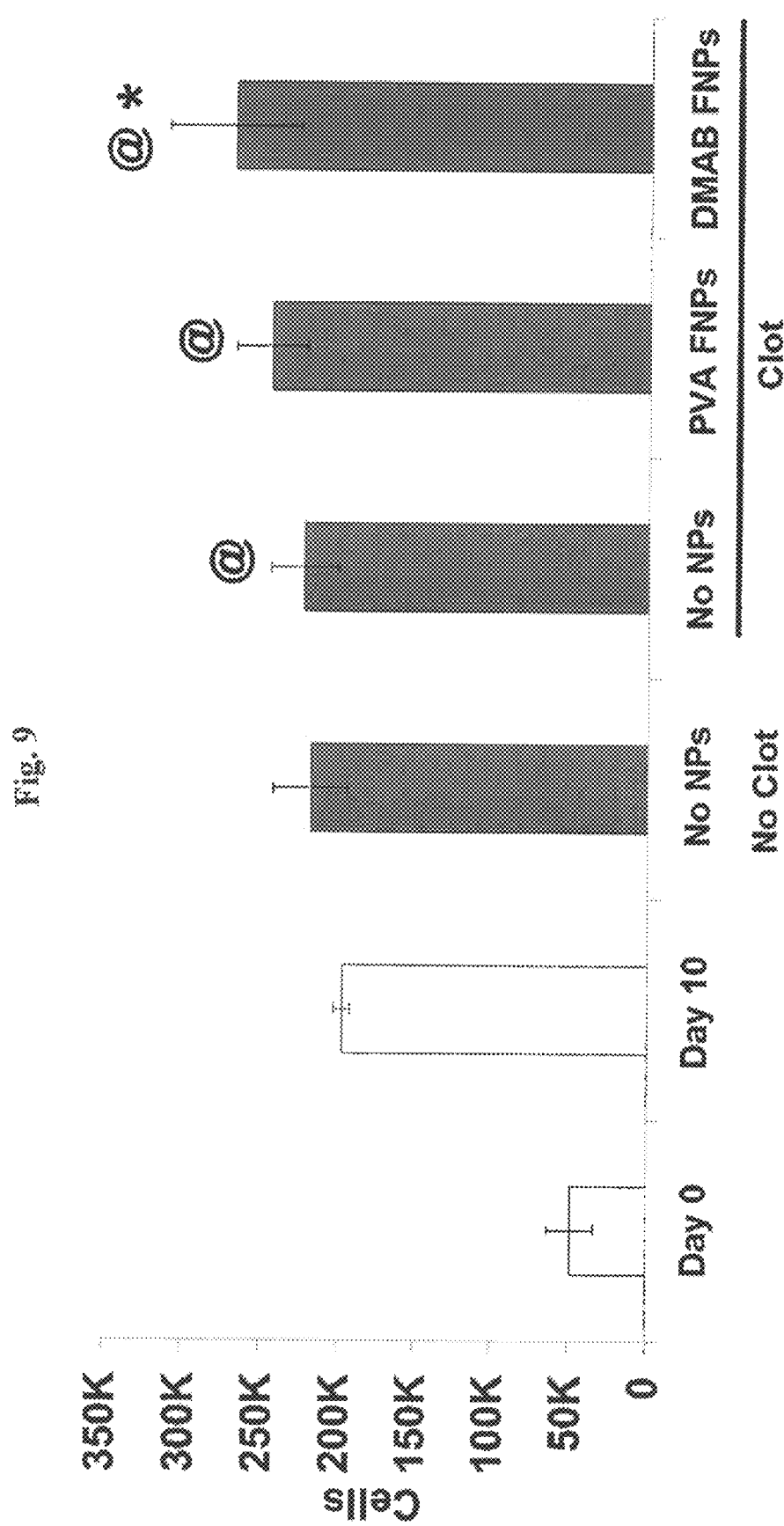
FIG. 9 provides a graph showing the proliferation of aneurysmal SMCs (EaRASMCs) in response to tPA and clot lysis products released following lysis of a fibrin clot by PVA- and DMAB-FNPs at 0.5 mg/mL NP concentration in a transwell culture (Clot+NPs in insert, EaRASMCs in wells). The cell number was calculated based on an estimate of 6 pg of DNA per cell, via a DNA assay, at 0, 10 and 21 days post-seeding, (mean±SD; n=6 per case, * denotes p<0.05 compared to unlysed clot control (Clot, No NP); @ denotes p<0.05 compared to day 10).

Effects of clot lysis products on proliferation and elastic matrix deposition by cultured EaRASMCs. FIG. 9 shows proliferation of seeded EaRASMCs over 21 days of culture. While there was no significant increase in cell number in control EaRASMC cultures, (no clot, no NP), EaRASMC proliferation was increased in the presence of an unlysed clot, and more significantly ($p<0.05$) when exposed to tPA released from the DMAB-FNPs, and products generated by tPA lysis of the fibrin clot.

Figure 10:
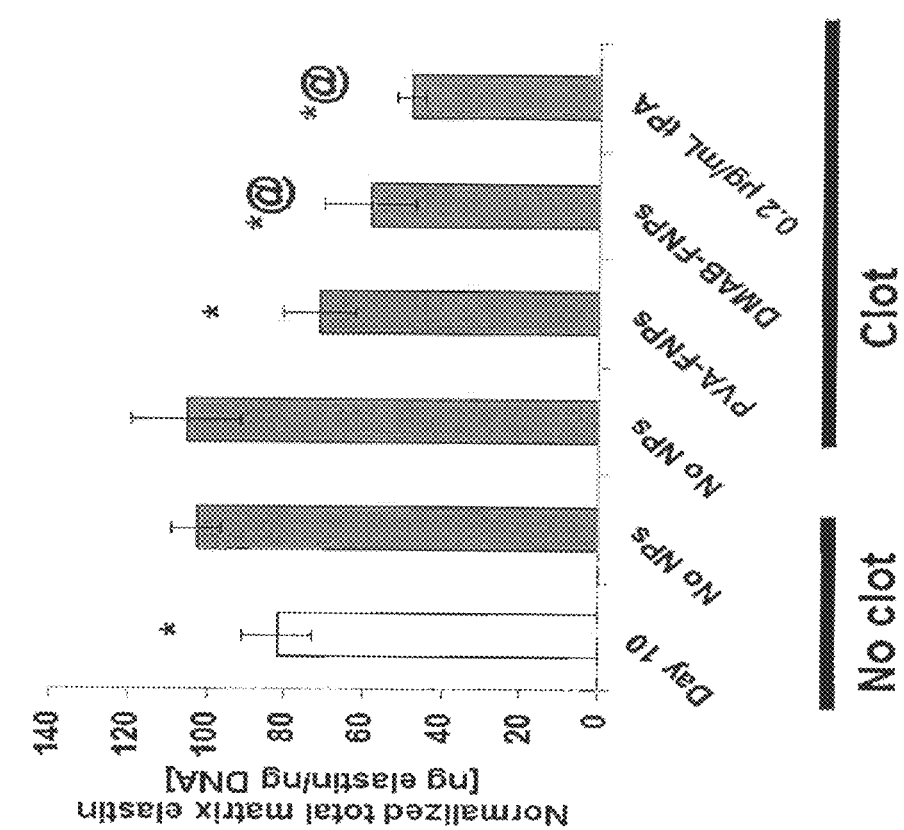
FIG. 10 provides a graph showing the effects of tPA and fibrinolytic products released following lysis of a fibrin clot by PVA- and DMAB-FNPs at 0.5 mg/mL NP concentration, as well as exogenous tPA (0.2 µg/mL; equivalent to the steady state concentration of tPA released from the FNPs) in a transwell culture (Clot+NPs and clot+exogenous tPA in insert, EaRASMCs in wells) on net elastic matrix deposition and/or preservation (A) on an absolute basis and (B) normalized to DNA content. (mean±SD; n=6/case, * denotes p<0.05 compared to unlysed clot control (No Clot, No NP), @ denotes p<0.05 compared to day 10 baseline; Note: EaRASMCs were cultured for a total of 21 days—the initial 10 days to allow them to deposit measurable amounts of elastic matrix (which we used as a baseline), followed by 11 days in the presence of a fibrin clot and FNPs, as well as exogenous tPA.
Figure 10:
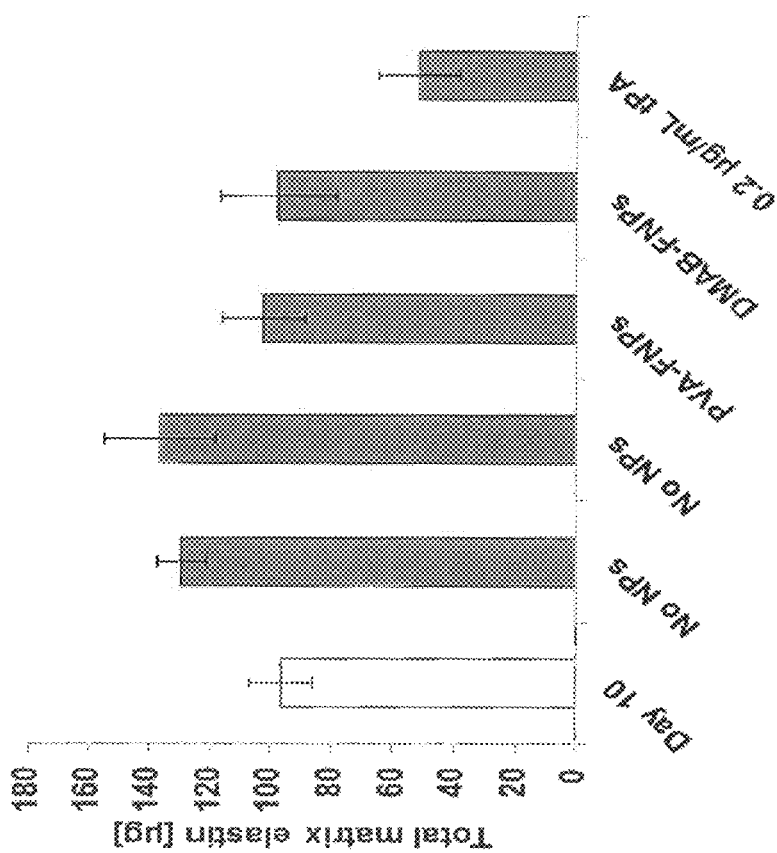

A significant increase ($p<0.05$) in total elastic matrix deposition in control EaRASMC cultures at day 21 compared to day 10 was observed, both on an absolute basis (FIG. 10A) and a per cell basis (FIG. 10B). There was no significant difference ($p>0.05$) in elastic matrix deposition between EaRASMCs cultured in the presence and absence of a fibrin clot. However, both DMAB- and PVA-FNP-mediated clot lysis prevented further increases in elastic matrix amounts within EaRASMC cultures, different from EaRASMCs cultured in the presence of an unlysed clot ($p<0.05$) (FIGS. 10A and B). In EaRASMC cultures exposed to DMAB-FNP lysed clots, the DNA-normalized total elastic matrix amounts measured at 21 days of culture was significantly lower ($p<0.05$) than that measured in the cell layers at 10 days post-seeding, even prior to exposure to the fibrin clot (FIG. 10B). FIG. 10 also shows that that clot lysis following controlled delivery of tPA from these polymeric nanoparticles is significantly advantageous over that following bulk/exogenous delivery of (an equivalent dose) of tPA to a fibrin clot, from the standpoint of (a) slower lysis to prevent loss of the biomechanical shielding effect of the clot (in AAAs) and also prevent sudden exposure of the underlying AAA wall to inflammatory cells and proteases and (b) preserving/regenerating elastic matrix.

Effects of fibrinolytic products on MMP synthesis and activity. Western blots showed MMP-2 protein synthesis in standalone EaRASMC cultures (no clot, no NP) to be significantly lower (1.6 fold; $p<0.05$) than in cultures exposed to unlysed clots (FIGS. 11A and B). tPA released from NPs and the products of fibrin clot lysis by this tPA collectively did not induce any significant increase in MMP-2 synthesis compared to cell layers cultured in the presence of an unlysed clot (p>0.05). In all cases, MMP-9 bands were absent or too faint to be quantified reliably via densitometry.

Figure 11:
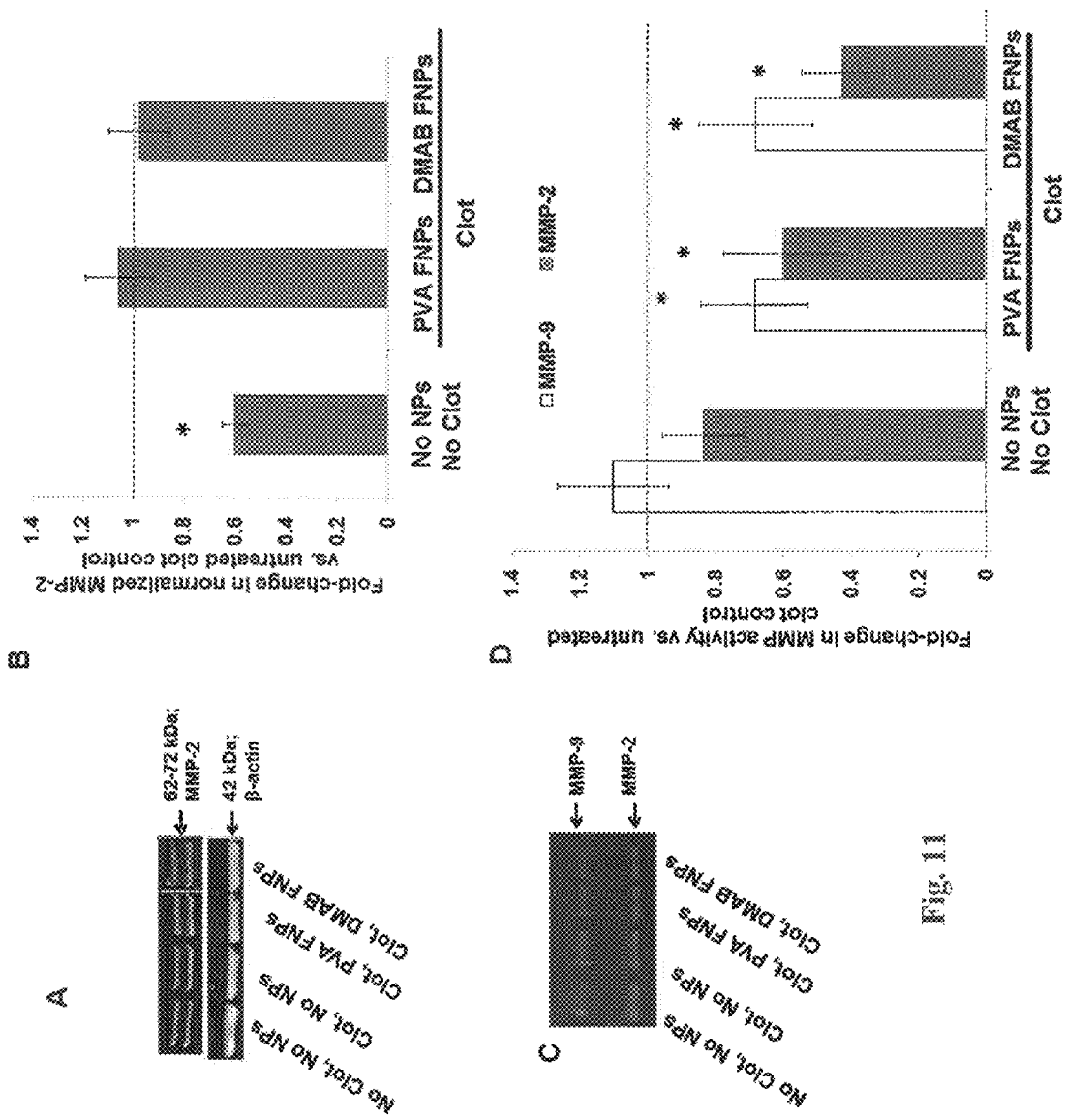
FIG. 11 shows effects of tPA and fibrinolytic products released following lysis of a fibrin clot by PVA- and DMAB-FNPs at 0.5 mg/mL NP concentration in a transwell culture (Clot+NPs in insert, EaRASMCs in wells) on (A, B) MMP-2 synthesis and (C, D) MMP-2 and -9 activity in EaRASMC cultures, as analyzed with western blots and gel zymography, respectively. (A) Representative image of western blot, with β-actin bands as loading controls. (B) Fold-change in production of MMP-2 compared to control cultures without NPs. (C) Representative image of gel zymogram, showing MMP-2 and -9 bands. (D) Fold-change in MMP-2 activity compared to NP-untreated control EaRASMC cultures. Data represented (mean±SD; n=3/case for western blots and gel zymograms, * denotes p<0.05 compared to unlysed clot control (No Clot, No NP). Notes: Values in FIG. 6B represent the fold-change in normalized band intensities of the active MMP-2 band for each treatment test case (normalized to its corresponding β-actin loading control band to enable accurate comparison between the different test cases) compared to unlysed (No Clot, No NP) controls. The normalized band intensity of MMP-2 for the NP-untreated control test condition was set to unity to determine fold-change in MMP-2 expression or activity for the different NP-treated test cases.

Gel zymograms showed faint bands for MMP-9, along with more prominent bands for MMP-2, as seen in FIG. 11C. Densitometric analysis showed MMP-2 and -9 activities in EaRASMC layers not exposed to clots were found to not be significantly lower (p>0.05) than in cultures exposed to the unlysed clots. However, MMP-2 and -9 activities in EaRASMC layers exposed to NP-released tPA and lysis products from DMAB- and PVA-FNP lysed fibrin clots were significantly lower (p<0.05), compared to the unlysed clot controls.

Effects of clot lysis products on plasmin activity. As seen in FIG. 12, the presence of an unlysed clot significantly enhanced plasmin activity (p<0.05) within the EaRASMC layer compared to the control EaRASMCs (no clot, no NP). However, upon lysis of the fibrin clot following tPA release from the NPs, a significant increase in plasmin activity within the EaRASMC layers (compared to the unlysed clot control) was observed. There were however no significant differences (p>0.05) in plasmin activity between cultures exposed to clots lysed with DMAB-FNPs and with PVA-FNPs.

Immunofluorescence detection of elastin in matrix. Confocal images for EaRASMC layers immunolabeled for elastin at the end of 21 days of culture with FNPs were obtained.

A representative image of the immunofluorescence control (untreated with primary antibodies) is included, which indicates the absence of any false fluorescence on account of any non-specific binding of the fluorescent secondary antibodies to the cell layer. The images of all culture groups show that there is significant deposition of both intra- and extra-cellular for the control clot culture.

Discussion

AAAs represent a proteolytic disease characterized by the degradation of the elastic matrix in the aortic wall, which leads to its progressive weakening and subsequent rupture. There is evidence that following its early loss, collagen in the AAA wall is regenerated by cells responding to higher perceived wall stresses, thereby stiffening the AAA wall and temporarily stabilizing its growth. As an agonist of platelets, collagen recruits platelets to form an intraluminal thrombus (ILT), the thickness of which has been shown to correlate positively with the extent of matrix disruption within the AAA wall. Thus, an ILT is present in 75% of AAAs (Sun et al., Br J Radiol. 82:S18-S23 (2009), and plays an important role in furthering proteolysis within the AAA wall, serving as a reservoir of inflammatory cells and proteases. Studies have shown that the AAA wall underlying an ILT is thinner and exhibits significantly disruption of the elastic matrix, lower density of SMCs and higher density of inflammatory cells, compared to ILT-free AAA tissue. (Kazi et al., J Vasc Surg. 38:1283-92 (2003)). As seen in the schematic in FIG. 1, proteases such as MMPs, thrombin, elastase & plasmin, which are generated within the ILT and also released by inflammatory cells (such as activated platelets & leukocytes) degrade the aortic wall matrix. (Touat et al., Am J Pathol. 168:1022-30 (2006)). These proteases also stimulate SMCs in the aortic wall to produce MMP-2 & plasminogen activators (PAs). In fact, MMPs form a mutually activating positive feedback system with thrombin. (Galis Z S. Molecular mechanisms of plaque weakening and disruption. In: Brown D, editor. Cardiovascular Plaque Rupture. New York, N.Y.: Marcel Dekker, Inc.; 2002. p. 79-121). The complementary localization of plasminogen (adsorbed from plasma and bound to fibrin) within the ILT and its activators in the AAA wall leads to plasmin generation, which in turn leads to further MMP activation & wall matrix degradation. (Carmeliet et al., Nat Genet., 17:439-44 (1997)).

The ILT also serves as a barrier for the delivery of oxygen and nutrients to the underlying aortic wall, thereby adversely affecting viability of medial SMCs and leading to further progression of AAA pathology. Since the ILT also mechanically shields the underlying AAA wall from high hemodynamic stresses (Di Martino et al., Eur J Vasc Endovasc Surg, 15:290-9 (1998)), the inventors hypothesize that eliminating it slowly from the AAA site will be important to halt its contribution to proteolytic events within the AAA wall, and enable delivery of therapeutic agents (as well as nutrients and oxygen) to the AAA wall, while maintaining its stabilizing effects. Therefore, there is a significant motivation to develop modalities for controlled and gradual lysis of ILTs within AAAs.

In recent years, fibrinolytic agents such as streptokinase and tPA have been administered via the intravenous route, to dissolve endoluminal blood clots to recanalize the vessel and restore blood flow in patients suffering from strokes (Shaltoni et al., Stroke. 38:80-4 (2007)) and myocardial infarctions (Andersen et al., N Engl J Med., 349:733-42 (2003)). However, systemic fibrinolytic therapy can have adverse side effects, particularly in the form of uncontrolled bleeding, which is typically associated with depletion of circulating fibrinogen, the main plasma clotting protein. Encapsulation of these agents within liposomes and polymeric microcarriers (Leach et al., Thromb Haemost. 90:64-70 (2003)) have been shown to enhance the efficacy of thrombolysis in vitro and in vivo, due to the ability of these carriers to infiltrate into the thrombus (Wu et al., Thromb Haemost., 72:105-12 (1994)), and also protect tPA from inactivation by PA-inhibitors (PAI) present in circulation. Permeation of these carriers into the thrombus and their localized release of tPA can facilitate homogenous intraclot lysis. (Collet et al., Arterioscler Thromb Vasc Biol., 20:1354-61 (2000)). This represents an improvement over the delivery of free tPA, which due to its affinity for fibrin, limits its effects to the narrow blood-thrombus interface. Additionally, tPA encapsulation has also been shown to reduce the total exposure time of tPA to the plasma proteins within the bloodstream relative to systemically delivered free tPA, thereby preventing depletion of fibrinogen levels within the bloodstream (a critical component in maintenance of hemostasis) and consequent bleeding complications.

Most studies involving delivery of encapsulated tPA have aimed at achieving rapid thrombolysis, which would be highly desirable from the perspective of treating stroke or MI. However, from the standpoint of targeting the ILT within AAAs, gradual thrombolysis will be required, to (a) minimize bleeding issues, while (b) avoiding potential embolic complications from rapid, non-uniform thrombolysis, and (c) attenuate plasmin generation and subsequent MMP-activation in order to preserve and/or regenerate elastic matrix structure within the AAA wall. These factors motivated our development of novel nanotherapeutics for localized gradual clot lysis within AAAs.

PLGA NPs have been widely used as drug carriers, as PLGA has been approved by the U.S. Food and Drug Administration (FDA) for clinical drug delivery applications, due to its biodegradability and suitable biodegradation characteristics, its biocompatibility when used in conjunction with a range of drugs, and ease of formulation. (Lu et al., Expert Rev Mol Diagn. 9:325-41 (2009)). PLGA NPs have been used in previous studies by other groups for the encapsulation and delivery of tPA, however, it must be noted these studies were focused on achieving rapid thrombolysis. (Wang S-S et al., J Biomed Mater Res. 91A:753-61 (2009)). The inventors utilized PLGA containing a 50:50 lactide: glycolide ratio in these studies, since this is the predominant form of PLGA used in drug delivery and other nanotechnology-based applications. Additionally, since high molecular weight PLGA degrades more slowly compared to low molecular PLGA, translating to more controlled drug release, the PLGA we used had a relatively high inherent viscosity of 0.95-1.2 dL/g (molecular weight=117.7 kDa, as per the manufacturer's specifications).

The PLGA NPs formulated had mean hydrodynamic diameters of ~375 nm (PVA-FNPs) and ~450 nm (DMAB-FNPs), which lies in the size range that we have shown earlier to be excluded in the extracellular space. (Sivaraman B, Ramamurthi A., Acta Biomater., 9:6511-25 (2013)). These sizes are significantly smaller than the typical pore size (~4 μm) of a fibrin clot, which would allow non-clustered NPs to easily permeate into the clot. However, it must be noted that the ILT pore sizes in AAAs is highly variable (from few nm to μm; Gasser et al., Ann Biomed Eng., 38:371-9 (2010)), with patients with large AAAs exhibiting denser clots with smaller pores compared to those with small AAAs, rendering them more resistant to lysis. (Scott et al., Arterioscler Thromb Vasc Biol., 31:3004-10 (2011)). Thus, the NPs we have formulated would be expected to permeate to some extent within the ILT, and thereafter render the ILT more porous via clot lysis following tPA release from the NPs. The PLGA NPs formulated with PVA and DMAB exhibited surface charges (ζ-potentials) of −36 mV and +23 mV, respectively (Table 1). The inventors sought to create and evaluate both negatively- and positively-charged tPA-releasing NPs, since both provide their respective benefits in the current application. While the anionic PVA-FNPs would likely be distributed throughout the clot and cause homogenous clot lysis, cationic DMAB-FNPs would be expected to demonstrate enhanced binding to negatively-charged fibrin within the clot. Additionally, cationic NPs would also demonstrate enhanced arterial uptake (Labhasetwar et al., J Pharm Sci., 87:1229-34 (1998)), and also repel cationic elastases (Gertler A., Eur J Biochem., 20: 541-6 (1971)), while being multifunctional in terms of improving elastic matrix deposition and inhibiting MMPs, as shown earlier, thereby enabling enhanced elastic matrix preservation and/or regeneration within the AAA wall. The encapsulation of tPA within the NPs did not significantly affect their size or surface charge (Table 1).

Since a major goal was to prolong fibrinolysis, the amounts of tPA we loaded within our NPs was significantly lower than that encapsulated by other groups. The inventors' tPA encapsulation efficiencies were estimated to be greater than 90%, which was much higher than that obtained by other groups (65-70%; Chung et al., Biomaterials., 29:228-37 (2008)), and may be attributed to the fact that at lower tPA loadings, the amount of tPA included within the emulsion during the formulation process is higher and thus leads to higher encapsulation efficiency. (Narang, Int J Pharm., 345:9-25 (2007)). Consistent with earlier studies (Chung et al., Biomaterials., 29:228-37 (2008)), a burst of tPA release occurred during the initial 2 h, following which the release gradually plateaued to attain steady-state at 48 h (FIG. 6). While the burst release of tPA can be attributed to the rapid out-diffusion of tPA near the NP surface upon solubilization by the infiltrating aqueous medium, and is driven by the high concentration gradient (of tPA), the steady state release phase corresponds to slow diffusion driven by a much reduced concentration gradient, with the tPA release rate being limited by the slow hydrolysis of the PLGA matrix. Although the burst release of tPA may be of concern from the standpoint of rapid clot lysis, this was not observed with our NPs, likely because the tPA released over the initial 2 h represented only <10% of that theoretically encapsulated. The inventors results also showed that the burst release and steady-state tPA concentrations for tPA release from PVA-FNPs to be higher than that for DMAB-FNPs. Since the encapsulation efficiencies for both formulations were very similar (>90%), the higher release from the PVA-FNPs is likely due to their smaller size, which would result in a higher surface area per unit volume for these NPs, leading to higher out-diffusion of tPA.

Figure 7:
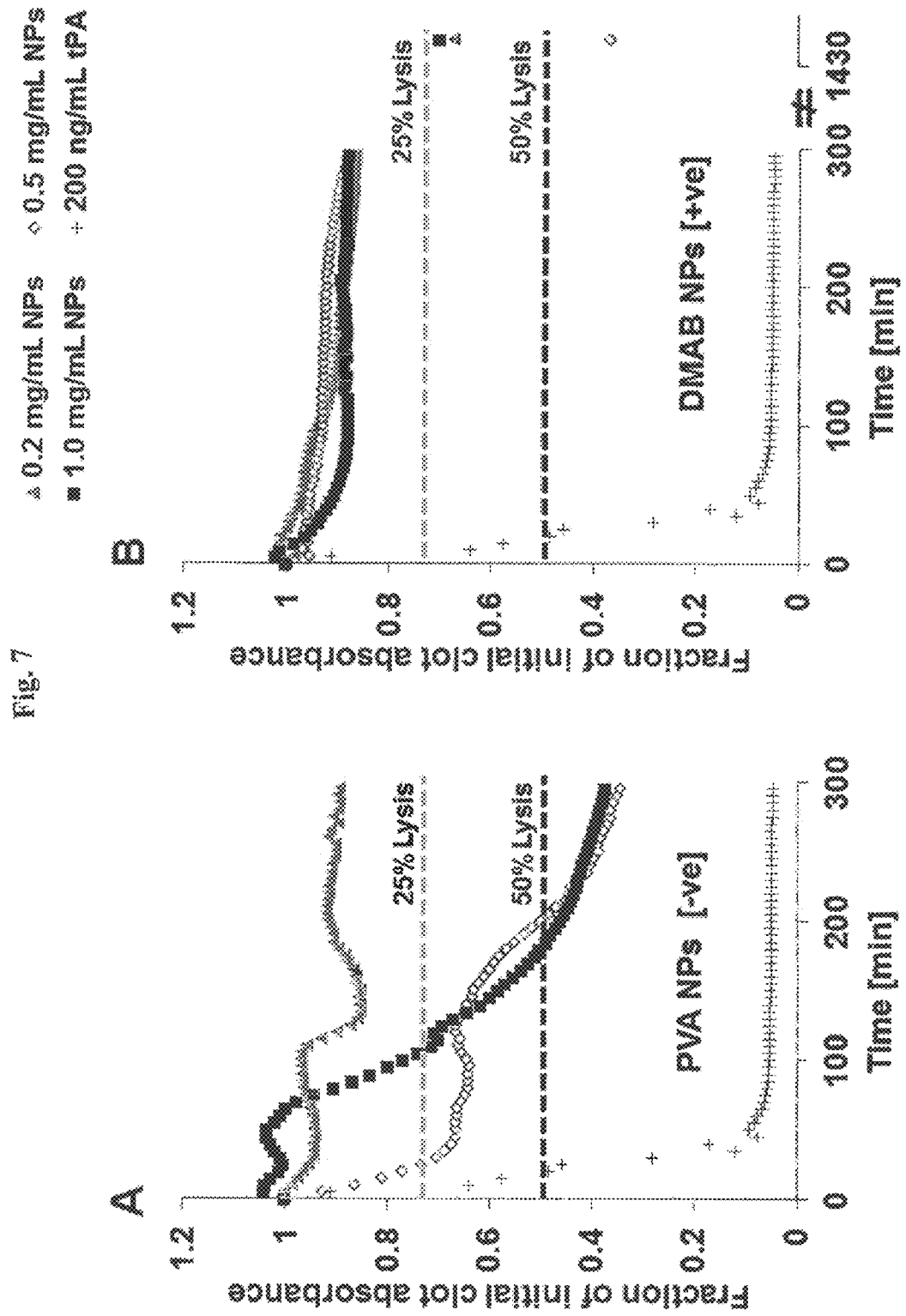
FIG. 7 provides graphs showing the lysis profiles of fibrin clots incubated with (A) PVA- and (B) DMAB-FNPs (loaded with 10 µg of tPA), at 0.2, 0.5 and 1.0 mg/mL NP concentrations, with 200 ng/mL of tPA solution as the exogenous control. The absorbance of the NP-lysed clot (at 405 nm), calculated by subtracting the absorbances of control wells (containing only NPs) from that of wells containing the NPs with clot, was plotted as a fraction of its initial absorbance as a function of time. All values plotted are mean values of three different clots.

The rationale for the delivery of tPA from NPs is to be able to catalyze the conversion of plasminogen locally within the clot to plasmin, to efficiently cause fibrinolysis and clot lysis. (Wolberg A S., Blood Rev., 21:131-42 (2007)). While the inventors demonstrated this to be possible, at all tPA loadings and FNP concentrations tested, they observed that DMAB-FNPs demonstrated slower fibrinolysis, as observed by the decrease in fractional clot absorbance, compared to PVA-FNPs (FIG. 7). Although this could be due to the slower release of tPA from DMAB-FNPs compared to their PVA counterparts (FIG. 6), the inventors hypothesize that the more dominant effect underlying the more gradual fibrinolysis may be attributed to the positively charged DMAB-FNPs binding electrostatically to fibrin, which is negatively charged at pH 7.4, leading to their localization at the clot boundary/interface. PVA-FNPs on the other hand would be expected to permeate and become distributed throughout the clot, mediating more rapid intra-clot lysis unlike DMAB-FNPs which would primarily cause clot lysis to proceed as a front (i.e., outside to inside), in a top-down manner. Fibrin clot binding studies (FIG. 8) confirmed that DMAB-NPs bound to fibrin clots more strongly, compared to PVA-NPs. This differential ability of cationic NPs to bind fibrin within clots may thus be beneficial in enabling/enhancing NP targetability to clots.

Since FNPs loaded with 10 μg of tPA effectively extended fibrinolysis as desired, we utilized this formulation to investigate how the clot lysis products generated impacted elastic matrix preservation and assembly by aneurysmal rat aortic SMCs (EaRASMCs). Neither exposure to an unlysed clot nor exposure to FNP-released tPA and clot lysis products impacted EaRASMC proliferation (FIG. 9). EaRASMC proliferation was not significantly enhanced (p=0.06) in cultures exposed to tPA released by PVA-FNPs and its clot lysis products, compared to those exposed to an unlysed clot. However, tPA released from DMAB-FNPs and its clot lysis products increased EaRASMC proliferation significantly (p<0.05) compared to cultures exposed to an unlysed clot. This result was similar to that obtained by other groups who observed that tPA (Yang et al., J Vasc Surg. 42:532-8 (2005)), fibrin degradation products (Ahmann et al., Tissue Eng Part A., 16:3261-70 (2010)), and plasmin (Rortocil et al., Surgery. 138:180-6 (2005)) enhance vascular SMC proliferation. However, the exact mechanisms by which these biomolecules mediate this effect remain unclear, and must be explored in a future study.

EaRASMCs cultured in the presence of tPA released from PVA- and DMAB-FNPs and their fibrinolysis products showed lower elastic matrix deposition compared to control cultures exposed to an unlysed clot (FIG. 10A). However, when normalized to the cellular content (FIG. 10B), elastic matrix amounts in the 21 day old EaRASMC layers cultured with DMAB-FNP lysed clots were significantly lower even relative to EaRASMC cultures harvested at day 10, prior to clot formation and lysis. These results indicate that clot lysis products cause a decrease in net elastic matrix deposition in EaRASMC cultures. The mechanisms underlying these effects, specifically whether the decreased elastic matrix deposition is due to an inhibition of de novo elastin synthesis or alternatively due to degradation of already deposited elastic matrix is unclear. However, the net decrease in elastic matrix may be attributed to increased MMP synthesis/activity within EaRASMC cultures either, or the direct effects of plasmin in degrading ECM. (Chapman H A, Jr., Stone O L., Biochem J., 222:721-8 (1984)).

While western blots (FIG. 11A, B) showed that products of clot lysis induced by the FNPs did not cause a significant increase in MMP-2 synthesis by EaRASMCs, gel zymography (FIG. 11C, D) indicates that lysis products from both DMAB- and PVA-FNP lysed clots cause a significant attenuation of MMP-2 and -9 activities in EaRASMC cultures, compared to untreated control cell cultures as well as untreated clot control cultures. This data strongly suggests that the net decrease in elastic matrix deposition by EaRASMCs post-fibrinolysis, was likely not due an upregulated MMP-mediated matrix breakdown. Instead, the results in FIG. 12 show that the decrease in net elastic matrix deposition within the EaRASMC layers exposed to NP-mediated clot lysis products (FIG. 10) is due to the effects of the increase in plasmin activity within the cell layers.

CONCLUSIONS

Overall, the results demonstrate the feasibility of developing NP-based systems for controlled release of tPA towards gradual clot lysis as a strategy for AAA therapy. Cationic DMAB-NPs demonstrated enhanced affinity for fibrin clots compared to anionic PVA-NPs, which can be harnessed to enable and improve targetability of NPs to clots. Additionally, the DMAB-FNPs demonstrated more gradual fibrinolysis compared to PVA-FNPs, which the inventors attributed to their electrostatic binding with the fibrin clot. Although clot lysis led to an increase in EaRASMC proliferation, it also caused a moderate decrease in net elastic matrix deposition in EaRASMC cultures. In fact, a significant attenuation of MMP-2 and -9 activities following clot lysis with PVA- and DMAB-FNPs was observed, with no significant increase in MMP synthesis, suggesting that the decrease in elastic matrix deposition by EaRASMCs is due to their exposure to plasmin following fibrinolysis by the FNPs.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of controlled dissolving of a blood clot in a subject by administering to the subject a therapeutically effective amount of fibrinolytic nanoparticles comprising a polymeric core having a surface that is functionalized with a cationic amphiphilic compound, and a fibrinolytic agent dispersed within the core, wherein the particle has a surface charge from +20 mV to +40 mV, wherein the method takes at least 2 hours to dissolve the blood clot.

2. The method of claim 1, wherein the polymeric core of the fibrinolytic nanoparticles comprise poly(lactic-co-glycolic acid).

3. The method of claim 1, wherein the fibrinolytic agent is tissue plasminogen activator.

4. The method of claim 1, wherein the cationic amphiphilic compound is didodecyldimethyl ammonium bromide.

5. The method of claim 1, wherein the fibrinolytic nanoparticle has a diameter from about 300 to about 500 nanometers.

6. The method of claim 1, wherein the fibrinolytic nanoparticles are delivered in a pharmaceutically acceptable carrier.

7. The method of claim 1, wherein the subject is human.

8. The method of claim 1, wherein the method takes at least 4 hours to dissolve the blood clot.

9. The method of claim 1, wherein the subject has been diagnosed as having an abdominal aortic aneurysm.

* * * * *